(12) United States Patent
Haffner et al.

(10) Patent No.: US 7,678,065 B2
(45) Date of Patent: Mar. 16, 2010

(54) IMPLANT WITH INTRAOCULAR PRESSURE SENSOR FOR GLAUCOMA TREATMENT

(75) Inventors: David S. Haffner, Mission Viejo, CA (US); Hosheng Tu, Newport Coast, CA (US); Morteza Gharib, San Marino, CA (US)

(73) Assignee: Glaukos Corporation, Laguna Hills, CA (US)

( * ) Notice: Subject to any disclaimer, the term of this patent is extended or adjusted under 35 U.S.C. 154(b) by 396 days.

(21) Appl. No.: 10/950,175

(22) Filed: Sep. 24, 2004

(65) Prior Publication Data
US 2005/0119636 A1    Jun. 2, 2005

Related U.S. Application Data

(63) Continuation-in-part of application No. 10/626,181, filed on Jul. 24, 2003, now Pat. No. 6,981,958, which is a continuation of application No. 09/847,523, filed on May 2, 2001, now Pat. No. 6,666,841.

(60) Provisional application No. 60/505,680, filed on Sep. 24, 2003.

(51) Int. Cl.
| A61B 5/00 | (2006.01) |
| A61B 5/04 | (2006.01) |
| A61B 5/103 | (2006.01) |
| A61B 5/117 | (2006.01) |
| G01L 27/00 | (2006.01) |
| G01L 7/08 | (2006.01) |
| G01L 7/10 | (2006.01) |
| G01L 7/02 | (2006.01) |

(52) U.S. Cl. ............... 600/561; 600/398; 600/587; 73/1.57; 73/715; 73/729.2; 73/730

(58) Field of Classification Search .............. 600/398, 600/561, 587; 73/1.57, 715, 729.2, 730
See application file for complete search history.

(56) References Cited

U.S. PATENT DOCUMENTS 3,788,327 A    1/1974  Donowitz et al.

(Continued)

FOREIGN PATENT DOCUMENTS

AU    200072059 A1    7/2001

(Continued)

OTHER PUBLICATIONS

International Search Report and Written Opinion in related International Application No. PCT/US05/33900, mailed Apr. 20, 2007, 14 pp.

(Continued)

*Primary Examiner*—Max Hindenburg
*Assistant Examiner*—Jeffrey G Hoekstra
(74) *Attorney, Agent, or Firm*—Knobbe Martens Olson & Bear LLP

(57) ABSTRACT

The invention discloses a trabecular stent and methods for treating glaucoma. The stent may incorporate an intraocular pressure sensor comprising a compressible element that is implanted inside an anterior chamber of an eye, wherein at least one external dimension of the element correlates with intraocular pressure. In some embodiments, the sensor may be coupled to the stent. Also disclosed are methods of delivery of the stent and the sensor to the eye.

10 Claims, 15 Drawing Sheets

U.S. PATENT DOCUMENTS

| | | |
|---|---|---|
| 4,037,604 A | 7/1977 | Newkirk |
| 4,168,697 A | 9/1979 | Cantekin |
| 4,175,563 A | 11/1979 | Arenberg et al. |
| 4,402,681 A | 9/1983 | Haas et al. |
| 4,428,746 A | 1/1984 | Mendez |
| 4,501,274 A | 2/1985 | Skjaerpe |
| 4,521,210 A | 6/1985 | Wong |
| 4,554,918 A | 11/1985 | White |
| 4,604,087 A | 8/1986 | Joseph |
| 4,632,842 A | 12/1986 | Karwoski et al. |
| 4,634,418 A | 1/1987 | Binder |
| 4,718,907 A | 1/1988 | Karwoski et al. |
| 4,722,724 A | 2/1988 | Schocket |
| 4,733,665 A | 3/1988 | Palmaz |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,936,825 A | 6/1990 | Ungerleider |
| 4,946,436 A | 8/1990 | Smith |
| 4,968,296 A | 11/1990 | Ritch et al. |
| 5,005,577 A | 4/1991 | Frenkel |
| 5,041,081 A | 8/1991 | Odrich |
| 5,073,163 A | 12/1991 | Lippman |
| 5,092,837 A | 3/1992 | Ritch et al. |
| 5,095,887 A | 3/1992 | Leon et al. |
| 5,127,901 A | 7/1992 | Odrich |
| 5,129,895 A | 7/1992 | Vassiliadis et al. |
| 5,171,213 A | 12/1992 | Price, Jr. |
| 5,178,604 A | 1/1993 | Baerveldt et al. |
| 5,180,362 A | 1/1993 | Worst |
| 5,246,451 A | 9/1993 | Trescony et al. |
| 5,290,295 A | 3/1994 | Querals et al. |
| 5,300,020 A | 4/1994 | L'Esperance, Jr. |
| 5,318,513 A | 6/1994 | Leib et al. |
| 5,334,137 A | 8/1994 | Freeman |
| 5,338,291 A | 8/1994 | Speckman et al. |
| 5,346,464 A | 9/1994 | Camras |
| 5,360,399 A | 11/1994 | Stegmann |
| 5,370,607 A | 12/1994 | Memmen |
| 5,370,641 A | 12/1994 | O'Donnell, Jr. |
| 5,372,577 A | 12/1994 | Ungerleider |
| 5,397,300 A | 3/1995 | Baerveldt et al. |
| 5,433,701 A | 7/1995 | Rubinstein |
| 5,454,796 A | 10/1995 | Krupin |
| 5,472,440 A | 12/1995 | Beckman |
| 5,476,445 A | 12/1995 | Baerveldt et al. |
| 5,486,165 A | 1/1996 | Stegmann |
| 5,516,522 A | 5/1996 | Peyman et al. |
| 5,520,631 A | 5/1996 | Nordquist et al. |
| 5,557,453 A | 9/1996 | Schalz et al. |
| 5,558,629 A | 9/1996 | Baerveldt et al. |
| 5,558,630 A | 9/1996 | Fisher |
| 5,562,641 A | 10/1996 | Flomenblit et al. |
| RE35,390 E | 12/1996 | Smith |
| 5,601,094 A | 2/1997 | Reiss |
| 5,601,549 A | 2/1997 | Miyagi |
| 5,626,558 A | 5/1997 | Suson |
| 5,626,559 A | 5/1997 | Solomon |
| 5,639,278 A | 6/1997 | Dereume et al. |
| 5,651,783 A | 7/1997 | Reynard |
| 5,665,114 A | 9/1997 | Weadock et al. |
| 5,670,161 A | 9/1997 | Healy et al. |
| 5,676,679 A | 10/1997 | Simon et al. |
| 5,681,275 A | 10/1997 | Ahmed |
| 5,702,414 A | 12/1997 | Richter et al. |
| 5,702,419 A | 12/1997 | Berry et al. |
| 5,704,907 A | 1/1998 | Nordquist et al. |
| 5,713,844 A | 2/1998 | Peyman |
| 5,723,005 A | 3/1998 | Herrick |
| 5,741,333 A | 4/1998 | Frid |
| 5,743,868 A | 4/1998 | Brown et al. |
| 5,752,928 A | 5/1998 | De Roulhac et al. |
| 5,766,243 A | 6/1998 | Christensen et al. |
| 5,785,674 A | 7/1998 | Mateen |
| 5,807,302 A | 9/1998 | Wandel |
| 5,810,870 A | 9/1998 | Myers et al. |
| 5,830,139 A | 11/1998 | Abreu |
| 5,830,171 A | 11/1998 | Wallace |
| 5,836,939 A | 11/1998 | Negus et al. |
| 5,840,041 A | 11/1998 | Petter et al. |
| 5,865,831 A | 2/1999 | Cozean et al. |
| 5,868,697 A | 2/1999 | Richter et al. |
| 5,879,319 A | 3/1999 | Pynson et al. |
| 5,882,327 A | 3/1999 | Jacob |
| 5,886,822 A | 3/1999 | Spitzer |
| 5,893,837 A | 4/1999 | Eagles et al. |
| 5,908,449 A | 6/1999 | Bruchman et al. |
| 5,932,299 A | 8/1999 | Katoot |
| 5,968,058 A | 10/1999 | Richter et al. |
| 5,981,598 A | 11/1999 | Tatton |
| 6,004,302 A | 12/1999 | Brierley |
| 6,007,510 A | 12/1999 | Nigam |
| 6,007,511 A | 12/1999 | Prywes |
| 6,033,434 A | 3/2000 | Borghi |
| 6,045,557 A | 4/2000 | White et al. |
| 6,050,970 A | 4/2000 | Baerveldt |
| 6,059,772 A | 5/2000 | Hsia et al. |
| 6,059,812 A | 5/2000 | Clerc et al. |
| 6,063,116 A | 5/2000 | Kelleher |
| 6,063,396 A | 5/2000 | Kelleher |
| 6,071,286 A | 6/2000 | Mawad |
| 6,077,299 A | 6/2000 | Adelberg et al. |
| 6,102,045 A | 8/2000 | Nordquist et al. |
| 6,123,668 A | 9/2000 | Abreu |
| 6,142,990 A | 11/2000 | Burk |
| 6,165,210 A | 12/2000 | Lau et al. |
| 6,168,575 B1 | 1/2001 | Soltanpour |
| 6,174,305 B1 | 1/2001 | Mikus et al. |
| 6,187,016 B1 | 2/2001 | Hedges et al. |
| 6,193,656 B1 | 2/2001 | Jeffries et al. |
| 6,197,056 B1 | 3/2001 | Schachar |
| 6,203,513 B1 | 3/2001 | Yaron et al. |
| 6,228,873 B1 | 5/2001 | Brandt et al. |
| 6,231,597 B1 | 5/2001 | Deem et al. |
| 6,241,721 B1 | 6/2001 | Cozean et al. |
| 6,254,612 B1 | 7/2001 | Hieshima |
| 6,266,182 B1 | 7/2001 | Morita |
| 6,268,398 B1 | 7/2001 | Ghosh et al. |
| 6,287,256 B1 | 9/2001 | Park et al. |
| 6,312,393 B1 | 11/2001 | Abreu |
| 6,342,058 B1 | 1/2002 | Portney |
| 6,375,642 B1 | 4/2002 | Grieshaber et al. |
| 6,423,001 B1 | 7/2002 | Abreu |
| 6,428,501 B1 | 8/2002 | Reynard |
| 6,443,893 B1 | 9/2002 | Schnakenberg et al. |
| 6,450,984 B1 | 9/2002 | Lynch et al. |
| 6,464,724 B1 | 10/2002 | Lynch et al. |
| 6,517,483 B2 | 2/2003 | Park et al. |
| 6,524,275 B1 | 2/2003 | Lynch et al. |
| 6,533,768 B1 | 3/2003 | Hill |
| 6,544,249 B1 | 4/2003 | Yu et al. |
| 6,579,235 B1 * | 6/2003 | Abita et al. .................. 600/398 |
| 6,585,680 B2 | 7/2003 | Bugge |
| 6,626,858 B2 | 9/2003 | Lynch et al. |
| 6,629,981 B2 | 10/2003 | Bui et al. |
| 6,638,239 B1 | 10/2003 | Bergheim et al. |
| 6,666,841 B2 | 12/2003 | Gharib et al. |
| 6,699,211 B2 | 3/2004 | Savage |
| 6,712,764 B2 | 3/2004 | Jeffries et al. |

| | | | |
|---|---|---|---|
| D490,152 S | 5/2004 | Myall et al. | |
| 6,736,791 B1 | 5/2004 | Tu et al. | |
| 6,780,165 B2 | 8/2004 | Kadziauskas et al. | |
| 6,783,544 B2 | 8/2004 | Lynch et al. | |
| 6,796,942 B1 | 9/2004 | Kreiner et al. | |
| 6,890,300 B2 | 5/2005 | Lloyd et al. | |
| 6,926,670 B2 | 8/2005 | Rich et al. | |
| 6,939,299 B1 | 9/2005 | Petersen et al. | |
| 2002/0013546 A1 | 1/2002 | Grieshaber et al. | |
| 2002/0133168 A1 | 9/2002 | Smedley et al. | |
| 2002/0143284 A1 | 10/2002 | Tu et al. | |
| 2002/0169130 A1 | 11/2002 | Tu et al. | |
| 2002/0188308 A1 | 12/2002 | Tu et al. | |
| 2003/0060752 A1 | 3/2003 | Bergheim et al. | |
| 2003/0088260 A1 | 5/2003 | Smedley et al. | |
| 2003/0097151 A1 | 5/2003 | Smedley et al. | |
| 2003/0120200 A1 | 6/2003 | Bergheim et al. | |
| 2003/0181848 A1 | 9/2003 | Bergheim et al. | |
| 2003/0187384 A1 | 10/2003 | Bergheim et al. | |
| 2003/0187385 A1 | 10/2003 | Bergheim et al. | |
| 2003/0229303 A1 | 12/2003 | Haffner et al. | |
| 2004/0024345 A1 | 2/2004 | Gharib et al. | |
| 2004/0050392 A1 | 3/2004 | Tu et al. | |
| 2004/0102729 A1 | 5/2004 | Haffner et al. | |
| 2004/0111050 A1 | 6/2004 | Smedley et al. | |
| 2004/0127843 A1 | 7/2004 | Tu et al. | |
| 2005/0159660 A1 | 7/2005 | Montegrande et al. | |
| 2007/0032734 A1 | 2/2007 | Najafi et al. | |
| 2007/0112263 A1 | 5/2007 | Fink et al. | |
| 2007/0123767 A1 | 5/2007 | Montegrande et al. | |
| 2007/0129623 A1 | 6/2007 | Fleischman et al. | |

FOREIGN PATENT DOCUMENTS

| | | |
|---|---|---|
| CA | 2244646 | 2/1999 |
| DE | 198 40 047 A1 | 3/2000 |
| EP | 0 858 788 A1 | 8/1998 |
| EP | 0 898 947 A2 | 3/1999 |
| EP | 1 114 627 A1 | 7/2001 |
| FR | 2 710 269 | 3/1995 |
| GB | 2 296 663 A | 7/1996 |
| JP | 11-123205 | 5/1999 |
| WO | WO 89/00869 | 2/1989 |
| WO | WO 91/18568 | 12/1991 |
| WO | WO 92/19294 | 11/1992 |
| WO | WO 94/13234 | 6/1994 |
| WO | WO 94/21205 | 9/1994 |
| WO | WO 95/08310 | 3/1995 |
| WO | WO 98/30181 | 7/1998 |
| WO | WO 98/35639 | 8/1998 |
| WO | WO 99/26567 | 6/1999 |
| WO | WO 99/30641 | 6/1999 |
| WO | WO 99/38470 | 8/1999 |
| WO | WO 00/13627 | 3/2000 |
| WO | WO 00/64389 | 11/2000 |
| WO | WO 00/64390 | 11/2000 |
| WO | WO 00/64391 | 11/2000 |
| WO | WO 00/64393 | 11/2000 |
| WO | WO 00/72788 | 12/2000 |
| WO | WO 01/50943 | 7/2001 |
| WO | WO 01/78631 | 10/2001 |
| WO | WO 01/78656 | 10/2001 |
| WO | WO 03/015659 | 2/2003 |
| WO | WO 03/073968 | 9/2003 |

OTHER PUBLICATIONS

International Preliminary Report on Patentability in related International Application No. PCT/US05/33900, mailed May 10, 2007, 7 pp.
PCT Publication—WO 01/50943, International Publication Date Jul. 19, 2001.
Detlev Spiegel, 7 Chirurgische Glaukomtherapie, pp. 79-88. (English translation enclosed.).
L. Jay Katz, M.D., A Call for Innovative Operations for Glaucoma, Arch Ophthalmology, Mar. 2000, vol. 118, pp. 412-413.
Anselm Kampik and Franz Grehn, Nutzen und Risiken augenärztlicher Therapie, Hauptreferate der XXXIII. Essener Fortbildung Für Augenärzte, Dec. 1998. (English translated version enclosed "Benefits and Risks of Ophthalmological Therapy.").
Phillip C. Jacobi, MD, Thomas S. Dietlein, MD, and Gunter K. Krieglstein, MD., Goniocurettage for Removing Trabecular Meshwork: Clinical Results of a New Surgical Technique in Advanced Cronic Open-Angle Glaucoma, American Journal of Ophthalmology, May 1999, pp. 505-510.
Philip C. Jacobi, MD, Thomas S. Dietlein, MD, and Gunter K. Krieglstein, MD., Bimanual Trabecular Aspiration in Pseudoexfoliation Glaucoma, Ophthalmology, 1998, vol. 105, No. 5, May 1998, pp. 886-894.
Phillip C. Jacobi, MD, Thomas S. Dietlein, MD, and Gunter K. Krieglstein, MD., Microendoscopic Trabecular Surgery in Glaucoma Management, Ophthalmology, 1999, vol. 106, No. 3, pp. 538-544.
Arthur L. Schwartz, MD, and Douglas R. Anderson, MD, Trabecular Surgery, Arch Ophthalmol, vol. 92, Aug. 1974, pp. 134-138.
R.A. Hill, Q. Ren, D.D. Nguyen, L-H Liaw, and M.W. Berns, Free-Electron Laser (FEL) Ablation of Ocular Tissues, Lasesr Med Sci 1998, pp. 13:219-226.
Maurice H. Luntz, MD, and D.G. Livingston, B.SC., Trabeculotomy AB Externo and Trabeculectomy in Congenital and Adult-Onset Glaucoma, American Journal of Ophthalmology, Feb. 1977, vol. 83, No. 2, pp. 174-179.
W.M. Grant, MD, Further Studies on Facility of Flow Through the Trabecular Meshwork, A.M.A. Archives of Ophthalmololgy, Oct. 1958, vol. 60, pp. 523-533.
Richard A. Hill, MD, George Baerveldt, MD, Serdar A. Ozler, MD, Michael Pickford, BA, Glen A. Profeta, BS, and Michael W. Berns,PhD, Laser Trabecular Ablation (LTA), Laser in Surgery and Medicine, 1991, vol. 11, pp. 341-346.
Detlev Spiegel, MD, Karin Kobuch, MD, Richard A. Hill, MD, Ronald L. Gross, MD, Schlemm's Canal Implant: A New Method to Lower Intraocular Pressure in Patients With POAG, Ophthalmic Surgery and Lasers, Jun. 1999, vol. 30, No. 6, pp. 492-494.
Hans Hoerauf, Christopher Wirbelauer, Christian Scholz, Ralf Engelhardt, Peter Koch, Horst Laque, and Reginald Birngruber, Slit-Lamp-Adapted Optical Coherence Tomography of the Anteriuor Segment, Graefe's Arch Clin. Exp. Ophthalmol, May 1999, vol. 238, pp. 8-18.
Sumita Radhakrishnam, Andrew M. Rollins, Jonathan E. Roth, S. Yazddanfar, Volker Westphal, David Bardenstein, and Joseph Izatt, Real-Time Optical Coherence Tomography of the Anterior Segment at 1310 nm, Arch Ophthalmology, Aug. 2001, vol. 119, pp. 1179-1185.
I. Grierson, R.C. Howes, and Q. Wang, Age-related Changes in the Canal of Schlemm, Exp. Eye Res., 1984, vol. 39, pp. 505-512.
Luanna K. Putney, Cecile Rose T. Vibat, and Martha E. O'Donnell, Intracellular C1 Regulates Na-K-C1 Cotransport Activity in Human Trabecular Meshwork Cells, 1999 American Physiological Society, Sep. 1999, pp. C373 through C383.
Edited by Kevin Strange, Cellular and Molecular Physiology of Cell Volume Regulation, Library of Congress Cataloging In-Publication Data, CRC Press, Inc., Copyright 1994, pp. 312-321.
William Tatton, Ruth M.E. Chalmers-Redman, Ajay Sud, Steven M. Podos, and Thomas Mittag, Maintaining Mitochondrial Membrane Impermeability: An Opportunity for New Therapy In Glaucoma, Survey of Ophthalmology, vol. 45, Supplement 3, May 2001, pp. S277 through S283.
Robert W. Nickells, Apoptosis of Retinal Ganglion Cells in Glaucoma: An Update of the Molecular Pathways Involved in Cell Death, Survey of Ophthalmology, vol. 43, Supplement 1, Jun. 1999, pp. S-151 through S-161.
Grune & Stratton, Harcourt Brace Jovanovich Publishers, edited by J.E. Cairns, Glaucoma, vol. 1, Chapter 14, Anatomy of the Aqueous Outflow Channels, by Johannes W. Rohen, Copyright 1986, pp. 277-296.
Yasuhiro Matsumoto and Douglas H. Johnson, Trabecular Meshwork Phagocytosis in Glaucomatous Eyes, Ophthalmologica 1997, vol. 211, pp. 147-152.

M. Bruce Shields, MD, A Study Guide for Glaucoma: Aqueous Humor Dynamics, Copyright 1982, pp. 6-43.

M.A. Johnstone, R. Stegmann, and B.A. Smit, American Glaucoma Society, 12th Annual Meeting, Cylindrical Tubular Structures Spanning from Trabecular Meshwork Across SC, Laboratory Studies with SEM, TEM and Tracers Correlated with Clinical Findings, p. 39.

W.G. Tatton, Apoptotic Mechanisms in Neurodegeneration: Possible Relevance to Glaucoma, European Journal of Ophthalmology, Jan.-Mar. 1999, vol. 9, Supplement 1, pp. S22 through S29.

Hosheng Tu, U.S. Appl. No. 09/452,963, filed Dec. 2, 1999, entitled Expandable/Retractable Stent for Venous Valvular Annulus Use.

Philip C. Jacobi, MD, Thomas S. Dietlein, MD, and Gunter K. Krieglstein, MD., Bimanual Trabecular Aspiration in Pseudowdoliation Glaucoma, Ophthalmology, 1998, vol. 105, No. 5, May 1998, pp. 886- 894.

L. Jay Katz, M.D., A Call for Innovative Operations for Glaucoma, Arch Ophthalmology, Mar. 2000, vol. 118, pp. 412-413.

Troncoso, Manuel U., Tantalum implants for inducing hypotony, American Journal of Ophthalmology, vol. 32, No. 4, Apr. 1949, pp. 499-508 (11 pages).

Bucciarelli, Patrice D., Working Model is Next Step in Team's Long Journey to Commercial Product, Healthfirst, Business First of Louisville, Louisville.Bizjournals.com, Feb. 27, 2004.

Guttman, Cheryl , Continuous IOP Monitoring Possible with Microsensor: Implantable Device Aims to Overcome Deficiencies of Current Monitoring Techniques. (Improvement in Patient Management) (Intraocular Pressure), Ophthalmology Times, Oct. 15, 2003, as cited in HighBeam Research, http://www.highbeam.com/DocPrint.aspx?DocId=1G1:109595800.

Rizq, et al., Intraocular Pressure Measurement at the Choroid Surface: A Feasibility Study with Implications for Implantable Microsystems, Br J Ophthalmol 2001; 85:868-871, Jul. 2001.

Walter et al., Development of a Completely Encapsulated Intraocular Pressure Sensor, Ophthalmic Research 2000; 32:278-284.

* cited by examiner

IMPLANT WITH INTRAOCULAR PRESSURE SENSOR FOR GLAUCOMA TREATMENT

RELATED APPLICATIONS

The present application is a continuation-in-part of U.S. patent application Ser. No. 10/626,181, filed Jul. 24, 2003, entitled "Implant with Pressure Sensor for Glaucoma Treatment," Now U.S. Pat. No. 6,981,958, which is a continuation application of U.S. patent application Ser. No. 09/847,523, filed May 2, 2001, entitled "Bifurcatable Trabecular Shunt for Glaucoma Treatment," now U.S. Pat. No. 6,666,841, and claims benefit from U.S. Provisional Application No. 60/505,680 filed Sep. 24, 2003, entitled "Intraocular Pressure Sensor" the entireties of which are hereby incorporated by reference.

BACKGROUND OF THE INVENTION

The present invention generally relates to medical devices and methods for reducing intraocular pressure in the animal eye. More particularly, the present invention relates to the treatment of glaucoma by permitting aqueous humor to flow out of the anterior chamber through a surgically implanted pathway.

The human eye is a specialized sensory organ capable of light reception and able to receive visual images. The trabecular meshwork serves as a drainage channel and is located in the anterior chamber angle formed between the iris and the cornea. The trabecular meshwork maintains a balanced pressure in the anterior chamber of the eye by draining aqueous humor from the anterior chamber.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork allows the aqueous humor ("aqueous") to enter Schlemm's canal, which then empties into aqueous collector channels in the posterior wall of Schlemm's canal and then into aqueous veins, which form the episcleral venous system. Aqueous is a transparent liquid that fills the region between the cornea, at the front of the eye, and the lens. The aqueous is continuously secreted by the ciliary body around the lens, so there is a constant flow of aqueous from the ciliary body to the eye's front chamber. The eye's pressure is determined by a balance between the production of aqueous and its exit through the trabecular meshwork (major route) or uveal scleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Glaucoma is grossly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous from the anterior chamber of the eye. Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, or diseases such as hyperthyroidism that produce vascular congestion.

All current therapies for glaucoma are directed at decreasing intraocular pressure. Medical therapy includes topical ophthalmic drops or oral medications that reduce the production or increase the outflow of aqueous. However, these drug therapies for glaucoma are sometimes associated with significant side effects, such as headache, blurred vision, allergic reactions, death from cardiopulmonary complications, and potential interactions with other drugs. When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if the morbidity associated with trabeculectomy could be decreased. The current morbidity associated with trabeculectomy consists of failure (10-15%); infection (a life long risk of 2-5%); choroidal hemorrhage, a severe internal hemorrhage from low intraocular pressure, resulting in visual loss (1%); cataract formation; and hypotony maculopathy (potentially reversible visual loss from low intraocular pressure).

For these reasons, surgeons have tried for decades to develop a workable surgery for the trabecular meshwork.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Trabeculopuncture: Q-switched Neodymiun (Nd) YAG lasers also have been investigated as an optically invasive technique for creating full-thickness holes in trabecular meshwork. However, the relatively small hole created by this trabeculopuncture technique exhibits a filling in effect and fails.

Goniophotoablation/Laser Trabecular Ablation: Goniophotoablation is disclosed by Berlin in U.S. Pat. No. 4,846,172 and involves the use of an excimer laser to treat glaucoma by ablating the trabecular meshwork. This was demonstrated not to succeed by clinical trial. Hill et al. used an Erbium:YAG laser to create full-thickness holes through trabecular meshwork (Hill et al., Lasers in Surgery and Medicine 11:341-346, 1991). This technique was investigated in a primate model and a limited human clinical trial at the University of California, Irvine. Although morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage: This is an ab interno (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanulostomy (VC) and non-penetrating trabeculectomy (NPT) are two new variations of filtering surgery. These are ab externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous through the surgical opening will continue. The risk of placing a glaucoma drainage device also includes hemorrhage, infection, and diplopia (double vision).

Examples of implantable shunts and surgical methods for maintaining an opening for the release of aqueous from the anterior chamber of the eye to the sclera or space beneath the conjunctiva have been disclosed in, for example, U.S. Pat. No. 6,059,772 to Hsia et al. and U.S. Pat. No. 6,050,970 to Baerveldt.

All of the above embodiments and variations thereof have numerous disadvantages and moderate success rates. They involve substantial trauma to the eye and require great surgical skill in creating a hole through the full thickness of the sclera into the subconjunctival space. The procedures are generally performed in an operating room and have a prolonged recovery time for vision.

The complications of existing filtration surgery have inspired ophthalmic surgeons to find other approaches to lowering intraocular pressure.

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized.

As reported in Arch. Ophthalm. (2000) 118:412, glaucoma remains a leading cause of blindness, and filtration surgery remains an effective, important option in controlling the disease. However, modifying existing filtering surgery techniques in any profound way to increase their effectiveness appears to have reached a dead end. The article further states that the time has come to search for new surgical approaches that may provide better and safer care for patients with glaucoma.

SUMMARY OF THE INVENTION

There is a great clinical need for the treatment of glaucoma by a method that is faster, safer, and less expensive than currently available modalities, and by implanting a device having pressure sensing capability for transporting aqueous from the anterior chamber to Schlemm's canal.

Glaucoma surgical morbidity would greatly decrease if one were to bypass the focal resistance to outflow of aqueous only at the point of resistance, and to utilize remaining, healthy aqueous outflow mechanisms. This is in part because episcleral aqueous humor exerts a backpressure that prevents intraocular pressure from going too low, and one could thereby avoid hypotony. Thus, such a surgery would virtually eliminate the risk of hypotony-related maculopathy and choroidal hemorrhage. Furthermore, visual recovery would be very rapid, and the risk of infection would be very small, reflecting a reduction in incidence from 2-5% to about 0.05%.

Techniques performed in accordance with embodiments herein may be referred to generally as "trabecular bypass surgery." Advantages of the present invention include lowering intraocular pressure in a manner which is simple, effective, disease site-specific, and can potentially be performed on an outpatient basis.

In accordance with one embodiment, trabecular bypass surgery (TBS) creates an opening, a slit, or a hole through trabecular meshwork with minor microsurgery. TBS has the advantage of a much lower risk of choroidal hemorrhage and infection than prior techniques, and it uses existing physiologic outflow mechanisms. In some aspects, this surgery can potentially be performed under topical or local anesthesia on an outpatient basis with rapid visual recovery. To prevent "filling in" of the hole, a biocompatible elongated device is placed within the hole and serves as a stent. U.S. Pat. No. 6,638,239, the entire contents of which are incorporated herein by reference, discloses trabecular bypass surgery.

In accordance with one embodiment, a trabecular shunt for transporting aqueous humor is provided. The trabecular shunt includes a hollow, elongate tubular element, having an inlet section and an outlet section. In one embodiment, the outlet section includes two bifurcatable segments or elements, adapted to be positioned and stabilized inside Schlemm's canal. In another embodiment, the outlet section is an axially linear section prior to and during implantation, and becomes two bifurcated segments after implantation.

In one embodiment, the trabecular shunt is placed inside a delivery apparatus. When the trabecular shunt is deployed from the delivery apparatus into the eye, the two bifurcatable elements of the outlet section bifurcate in substantially opposite directions. In one embodiment, a deployment mechanism within the delivery apparatus includes a push-pull type plunger.

In another embodiment, a delivery applicator may be placed inside a lumen of the hollow, elongate tube of the trabecular shunt. The delivery applicator may include a deployment mechanism for causing the two bifurcatable elements of the outlet section to bifurcate. In some embodiments, the delivery applicator may be a guidewire, an expandable basket, an inflatable balloon, or the like.

In accordance with another embodiment, at least one of the two bifurcatable elements is made of a shape-memory material, such as Nitinol or a shape-memory plastic. The shape-memory material has a preshape and a shape-transition temperature, such that the shape-memory trabecular shunt bifurcates to its preshape when it is heated to above the shape-transition temperature. The preshape of the two bifurcatable elements material may be at an angle with respect to the inlet section, preferably between about 70 degrees and about 110 degrees. An external heat source may be provided, which is adapted for heating the shape-memory material to above the shape-transition temperature of the shape-memory material.

In some embodiments, the trabecular shunt may be made of one or more of the following materials: polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polyimide, polysilison, silicone, polyurethane, Nylon™, polypropylene, hydroxyapetite, precious metal, Nitinol, stainless steel, biodegradable materials, and biocompatible materials. Further, the outlet section of the trabecular shunt may be configured as a coil, mesh, spiral, or other appropriate configuration as will be apparent to those of skill in the art. Further, the outlet section of the trabecular shunt may be porous, semi-permeable, fishbone, and/or of a continuous, solid form. The outlet section of the trabecular shunt may have a cross-sectional shape that is elliptical (e.g., oval), round, circular, D-shape, semi-circular, or irregular (asymmetrical) shape.

In one embodiment, at least one of the two bifurcatable elements has a tapered distal end, adapted for insertion ease. The trabecular shunt may have its surface coated with a coating material selected from one or more of the following: polytetrafluoroethylene (e.g., Teflon™), polyimide, hydrogel, heparin, hydrophilic compound, anti-angiogenic factor, anti-proliferative factor, therapeutic drugs, and the like. The surface coating material may also provide a mechanism for site-specific therapies.

In one embodiment, the device of the invention may include a flow-restricting member for restricting at least one component in fluid. The flow-restricting member may be a filter comprising one or more filtration materials selected from the following: expanded polytetrafluoroethylene, cellulose, ceramic, glass, Nylon, plastic, fluorinated material, or the like. The flow-restricting member may advantageously be a filter selected from the following group of filter types: hydrophobic, hydrophilic, membrane, microporous, and non-woven. The flow-restricting member acts to limit or prevent the reflux of any undesired component or contaminant of blood, such as red blood cells or serum protein, from the aqueous veins into the anterior chamber. It is useful to restrict one or more of the following components or contaminants: platelets, red blood cells, white blood cells, viruses, bacteria, antigens, and toxins.

In some embodiments, the trabecular shunt may include a pressure sensor for measuring the pressure of the anterior chamber of an eye of a patient. The pressure sensor may further include an electromagnetic (e.g., radiofrequency) transmitter, for wirelessly transmitting pressure measurements to a pressure receiver outside the patient's body.

Some embodiments relate to an apparatus for measuring intraocular pressure. The apparatus may comprise a compressible chamber sized to be placed in the anterior chamber of an eye. The chamber may be configured to change in at least a first dimension in response to a change in intraocular pressure such that the change in the first dimension is indicative of the change in intraocular pressure. In some embodiments, a second dimension of the compressible chamber remains substantially constant during the change in intraocular pressure.

Some embodiments relate to a method of measuring intraocular pressure, the method comprising measuring a dimension of a compressible chamber located in the anterior chamber of an eye, the chamber configured to change in the dimension in response to a change in intraocular pressure.

Some embodiments relate to a method of monitoring intraocular pressure, the method comprising placing a compressible chamber into the anterior chamber of an eye, the chamber configured to change in at least one dimension in response to a change in intraocular pressure. Some embodiments further comprise measuring the at least one dimension to determine intraocular pressure.

Some embodiments relate to an intraocular pressure sensor comprising a compressible element that is implanted inside an anterior chamber of an eye, wherein at least one external dimension of the element is correlated to compressing pressure reading. The compressible element is anchored to a tissue of the eye, preferably to an iris of the eye, wherein the element is positioned without obstruction of vision.

In one embodiment, the element further comprises an interior enclosure filled with a compressible fluid, wherein the compressible fluid is a gas. In another embodiment, the compressible element comprises a shape of a sphere, an ellipsoid shape, a torus shape or other convenient shape. In still another embodiment, at least a portion of the surface of the compressible element is rendered radiopaque.

Some embodiments relate to an intraocular pressure sensor comprising an implanted compressible element having at least one external dimension and an external measuring means for remotely viewing and measuring the at least one external dimension of the element. In one embodiment, the external measuring means is a slit lamp, an ultrasound imaging apparatus, a laser light apparatus, or the like. In an alternate embodiment, the intraocular pressure sensor comprises an implanted compressible element having at least one external dimension and a measuring means for viewing and measuring the at least one external dimension of the element, wherein the measuring means is implanted or is one component of an implanted stent in an eye.

Some embodiments relate to a method for measuring an intraocular pressure of an eye, comprising: providing a compressible element that is implanted inside an anterior chamber of the eye, wherein at least one external dimension of the element is correlated to compressing pressure reading; implanting the element inside the eye; using an external measuring means for remotely viewing and measuring the at least one external dimension of the element; and calculating the intraocular pressure of the eye by correlating the measured external dimension to the compressing pressure reading.

Some embodiments relate to a method of providing a sensor and an implant in an eye for treatment and monitoring of glaucoma. The method may comprise providing a delivery device, the delivery device comprising at least one implant having an inlet and an outlet section, the inlet section being in fluid communication with the outlet section and configured to conduct fluid from the anterior chamber of an eye to Schlemm's canal. The method may further comprise positioning the at least one implant in the eye such that the inlet section is in the anterior chamber of the eye and the outlet section is in Schlemm's canal and positioning the sensor in the eye to measure the intraocular pressure of the eye.

Some embodiments relate to a trabecular stent system for glaucoma treatment, the stent system comprising: an elongate tubular implant extending between an anterior chamber and Schlemm's canal for transporting fluid from said anterior chamber to said Schlemm's canal of an eye; and an intraocular pressure sensor in association with the implant, said sensor comprising a compressible element, wherein at least one external dimension of the element is correlated to compressing pressure reading.

In another embodiment of the system for treating glaucoma, the system may comprise an implant that is configured such that, in use, the implant conducts fluid from the anterior chamber of an eye to the Schlemm's canal of the eye and a pressure sensor that is configured to be wholly implanted in the eye.

In a further embodiment, the trabecular stent system further comprises a signal transmitter, said transmitter transmitting a sensed signal from said sensor indicative of the sensed pressure to a receiver. In some embodiments, the receiver is located outside of the eye or inside the eye. In some embodiments, the signal comprises a radiofrequency signal.

Some embodiments relate to a system for treating glaucoma, comprising: an intraocular pressure sensor, said sensor comprising a compressible element, wherein at least one external dimension of the element is correlated to compressing pressure reading; an elongate tubular implant for transporting fluid between an anterior chamber and Schlemm's canal; and a delivery applicator, said intraocular pressure sensor and said implant being positioned within said delivery applicator for delivering into the anterior chamber for implantation.

Among the advantages of trabecular bypass surgery in accordance with the invention is its simplicity. The microsurgery may potentially be performed on an outpatient basis with rapid visual recovery and greatly decreased morbidity. There is a lower risk of infection and choroidal hemorrhage, and there is a faster recovery, than with previous techniques.

Further features and advantages of the present invention will become apparent to one of skill in the art in view of the Detailed Description that follows, when considered together with the attached drawings and claims.

DETAILED DESCRIPTION OF THE PREFERRED EMBODIMENT

FIGS. 1 to 13 illustrate an apparatus for the treatment of glaucoma by trabecular bypass surgery in accordance with the present invention.

Figure 1:
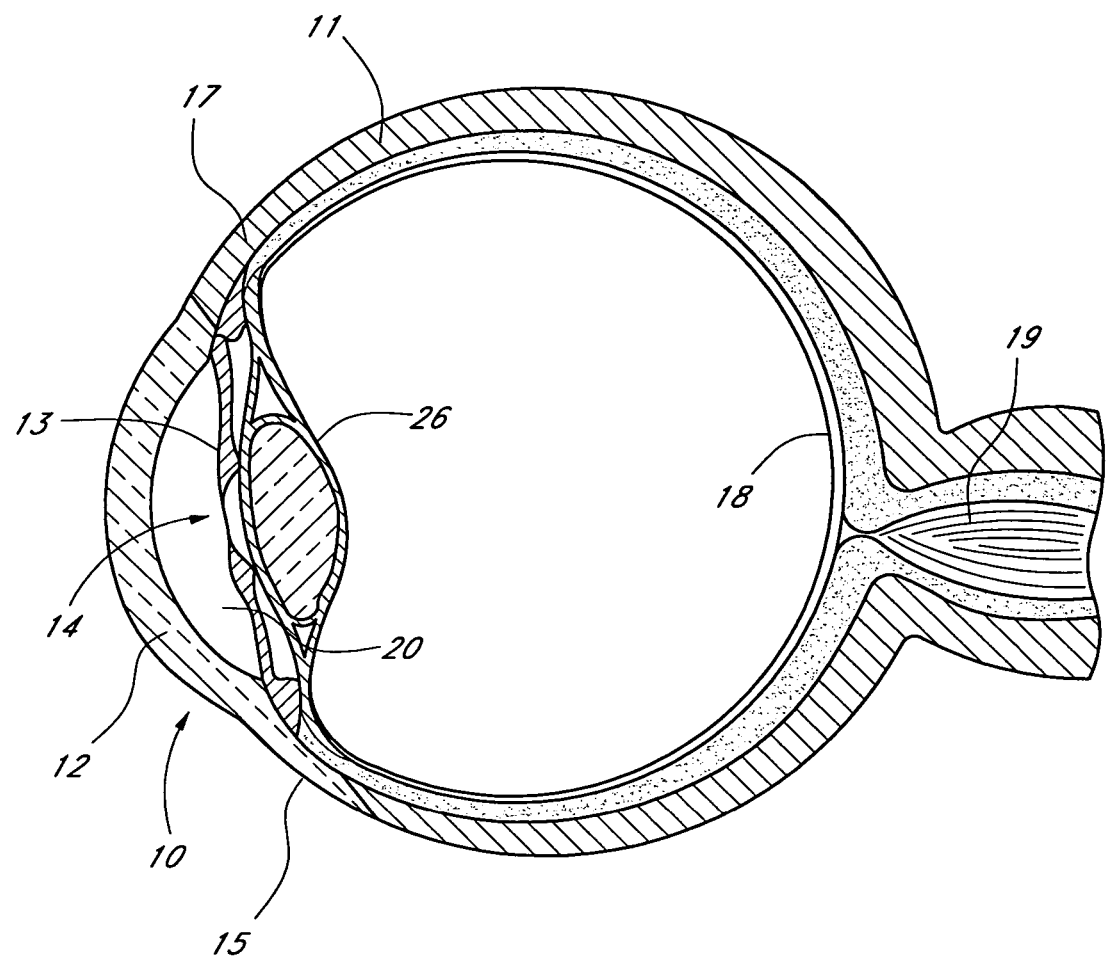
FIG. 1 is a sagittal sectional view of an eye.
Figure 2:
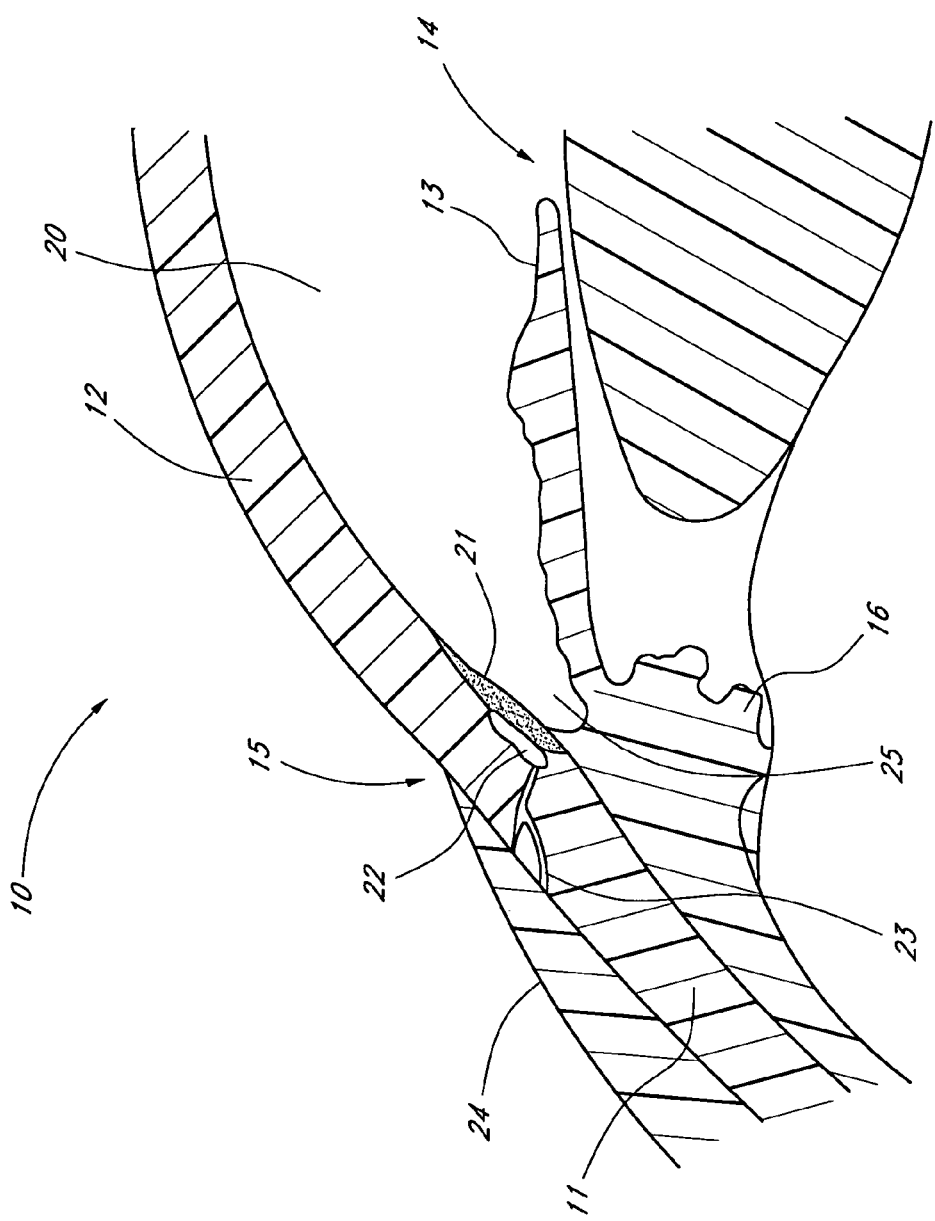
FIG. 2 is a cross-sectional view of the anterior chamber of an eye.

FIG. 1 is a sagittal sectional view of an eye 10, while FIG. 2 is a close-up view, showing the relative anatomical locations of trabecular meshwork 21, the anterior chamber 20, and Schlemm's canal 22. Thick collagenous tissue known as sclera 11 covers the entire eye 10 except that portion covered by the cornea 12. The cornea 12 is a thin transparent tissue that focuses and transmits light into the eye and through the pupil 14, which is the circular hole in the center of the iris 13 (colored portion of the eye). The cornea 12 merges into the sclera 11 at a juncture referred to as the limbus 15. The ciliary body 16 extends along the interior of the sclera 11 and is coextensive with the choroid 17. The choroid 17 is a vascular layer of the eye 10, located between the sclera 11 and retina 18. The optic nerve 19 transmits visual information to the brain and is the anatomic structure that is progressively destroyed by glaucoma.

The anterior chamber 20 of the eye 10, which is bound anteriorly by the cornea 12 and posteriorly by the iris 13 and lens 26, is filled with aqueous. Aqueous is produced primarily by the ciliary body 16, then moves anteriorly through the pupil 14 and reaches the anterior chamber angle 25, formed between the iris 13 and the cornea 12. In a normal eye, the aqueous is removed from the anterior chamber 20 through the trabecular meshwork 21. Aqueous passes through trabecular meshwork 21 into Schlemm's canal 22 and thereafter through the aqueous veins 23, which merge with blood-carrying veins and into systemic venous circulation. Intraocular pressure is maintained by the intricate balance between secretion and outflow of the aqueous in the manner described above. Glaucoma is, in most cases, characterized by the excessive buildup of aqueous in the anterior chamber 20, which leads to an increase in intraocular pressure. Fluids are relatively incompressible, and pressure is directed relatively equally throughout the eye.

As shown in FIG. 2, the trabecular meshwork 21 is adjacent a small portion of the sclera 11. Traditional procedures that create a hole or opening for implanting a device through the tissues of the conjunctiva 24 and sclera 11 involve extensive surgery, as compared to surgery for implanting a device which ultimately resides entirely within the confines of the sclera 11 and cornea 12, as is performed in accordance with one aspect of the present invention. In one embodiment, an outflow pathway is created that may operate to facilitate the flow of aqueous through or beyond the trabecular meshwork 21. A device 31 for establishing an outflow pathway, positioned through the trabecular meshwork 21, is illustrated in FIG. 8.

In one embodiment, a method of placing a trabecular shunt into an opening through trabecular meshwork, the method comprises advancing and positioning a trabecular shunt having two distal bifurcatable elements through the opening. In a further embodiment, a method of placing a trabecular shunt into an opening through diseased trabecular meshwork for transporting aqueous humor at the level of the trabecular meshwork and using an existing outflow pathway, the method comprises advancing and positioning a trabecular shunt having a pressure sensor for measuring the pressure of the anterior chamber of the eye through the opening. In one embodiment, the method may further comprise transmitting the measured pressure to a pressure receiver outside the body of the patient.

Abita et al. in U.S. Pat. No. 6,579,235, the entire contents of which are incorporated herein by reference, disclose a device and methods for measuring intraocular pressure of a patient including a sensor and an instrument external to the patient to determine the intraocular pressure.

Wolfgang et al. in U.S. Patent Application publication 2004/0116794, the entire contents of which are incorporated herein by reference, disclose a wireless intraocular pressure sensor device for detecting excessive intraocular pressure above a predetermined threshold pressure.

In a co-pending application Ser. No. 10/636,797 filed Aug. 7, 2003, entitled "Implantable Ocular Pump to Reduce Intraocular Pressure," the entire contents of which are incorporated herein by reference, an implant and a pressure sensor feedback system for regulating intraocular pressure of an eye is disclosed.

Montegrande et al. in U.S. Patent Application publication 2003/0225318, the entire contents of which are incorporated herein by reference, disclose an intraocular pressure sensor for sensing pressure within an eye and for generating a sensor signal representative of the pressure.

Jeffries et al., U.S. Patent Application publication 2003/0078487, the entire contents of which are incorporated herein by reference, disclose an intraocular pressure measuring system that includes a pressure sensor and an external device that wirelessly communicates with the pressure sensor.

Figure 3A:
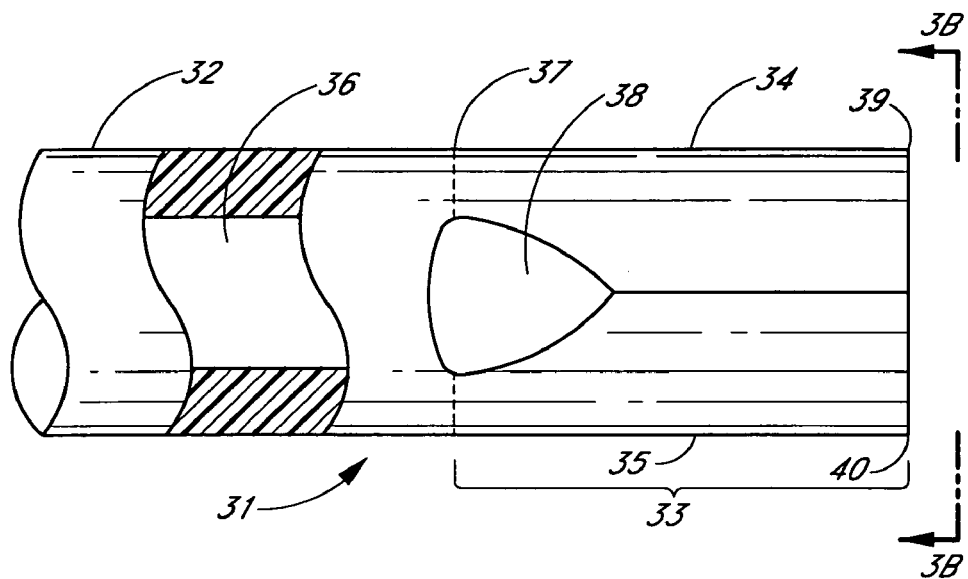
FIG. 3A is a side elevational view of a glaucoma device according to the present invention.

FIG. 3A shows an embodiment of the trabecular shunt 31 constructed according to the principles of the invention. The trabecular shunt may comprise a biocompatible material, such as medical grade silicone, trade name Silastic™, available from Dow Corning Corporation of Midland, Mich.; or polyurethane, trade name Pellethane™, also available from Dow Corning Corporation. In some embodiments, other biocompatible materials (biomaterials) may be used, such as polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polyimide, polysilison, silicone, polyurethane, Nylon, polypropylene, hydroxyapetite, precious metal, Nitinol, stainless steel, or any mixture of these or other biocompatible materials. In a further embodiment, the trabecular shunt may comprise a composite biocompatible material, with a surface made of one or more of the above-mentioned biomaterials, and the surface is coated by a material selected from Teflon, polyimide, hydrogel, heparin, hydrophilic compound, anti-angiogenic factor, anti-proliferative factor, therapeutic drugs, and the like. Suitable anti-angiogenic or anti-proliferative factors may be selected from, for example, protamine, heparin, steroids, anti-invasive factor, retinoic acids and derivatives thereof, and paclitaxel or its analogues or derivatives thereof.

The trabecular shunt transports aqueous at the level of the trabecular meshwork and partially uses existing the outflow pathway for aqueous, i.e., utilizing the entire outflow pathway except for the trabecular meshwork, which is bypassed by the trabecular shunt 31. In this manner, aqueous is transported into Schlemm's canal and subsequently into the aqueous collectors and the aqueous veins so that the intraocular pressure is properly maintained within a therapeutic range.

In one embodiment, the trabecular shunt 31 comprises a hollow, elongated tubular element having an inlet section 32 and an outlet section 33, wherein the outlet section 33 may comprise two bifurcatable elements 34, 35 that are adapted to be bifurcated, positioned, and stabilized inside Schlemm's canal. The hollow elongated tubular element may comprise at least one lumen 36 for transporting aqueous from the anterior chamber 20 of an eye to the Schlemm's canal 22. A "bifurcatable" segment is defined in the present invention as a segment, or components thereof, that can change direction away or evert from a reference axis. The "bifurcating" operation may be achieved by mechanical forces and/or through the shape-memory property of a material.

Figure 3B:
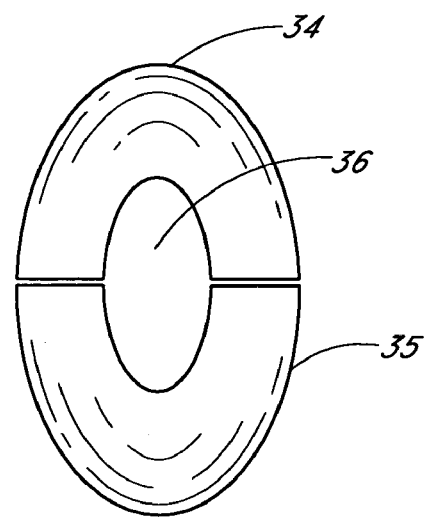
FIG. 3B is an end cross-sectional view through plane 1-1 of FIG. 3A.

For stabilization purposes, the outer surface of the outlet section 33 may comprise a stubbed surface, ribbed surface, a surface with pillars, textured surface, or the like. The outer surface of the trabecular shunt 31 is biocompatible and tissue-compatible so that the interaction between the outer surface of the shunt and the surrounding tissue of Schlemm's canal is minimal, and inflammation is reduced. FIG. 3B shows an end cross-sectional view of section 1-1 of FIG. 3A. Each bifurcatable segment 34, 35 has its own end configuration. At least one of the two bifurcatable elements has a tapered distal end adapted for insertion ease. The two bifurcatable elements 34, 35 are secured to the inlet section 32 at a joint 37. In an alternate embodiment, at least a slit 38, or scalloping, within the two bifurcatable elements 34, 35 may be located near the joint 37 for stress release when the two bifurcatable elements are bifurcated in two substantially opposite directions. Other stress-releasing mechanisms may also be utilized so as to make the bifurcation operation of the bifurcatable elements safe and effective. The outlet section 33 of the trabecular shunt 31 may possess a cross-sectional shape selected from the following: oval shape, round shape, circular shape, D-shape, semi-circular shape, irregular shape, or random shape.

In another embodiment, the trabecular shunt 31 may comprise a flow-restricting element for restricting at least one component in fluid, wherein the flow-restricting element may be a filter selected from a group of filtration materials comprising expanded polytetrafluoroethylene, cellulose, ceramic, glass, Nylon, plastic, and fluorinated material. Furthermore, the flow-restricting element may be a filter selected from a group of filter types comprising a hydrophobic filter, hydrophilic filter, membrane filter, microporous filter, non-woven filter, and the like. In accordance with the present invention, components in blood that may be restricted by the flow-restricting element can include the following: platelet, red blood cell, white blood cell, virus, antigen, serum protein, and toxin. The flow-restricting element may also be in the form of, for example, a check valve, a slit valve, a micropump, a semi-permeable membrane, and the like. The purpose of the flow-restricting element is to keep an undesired foreign material from back flowing into the anterior chamber.

Figure 4A:
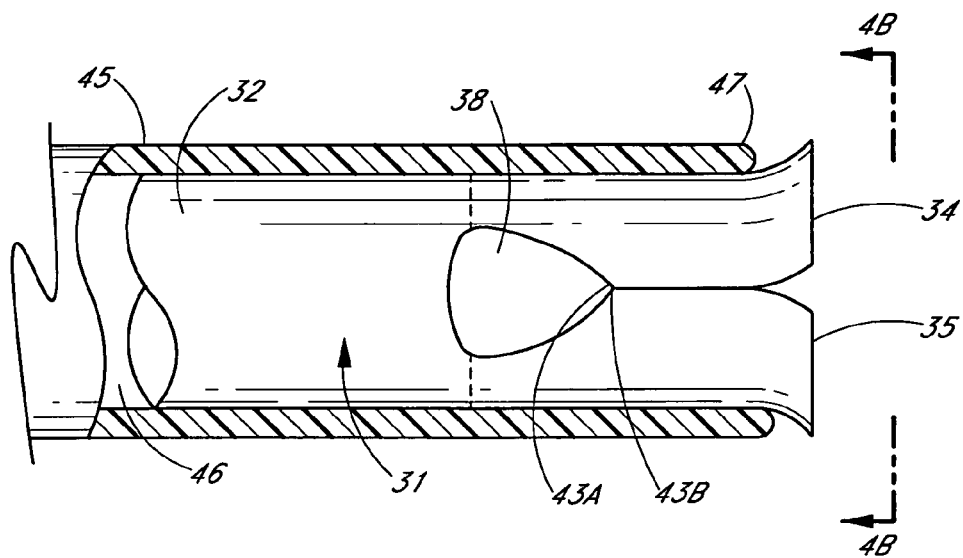
FIG. 4A illustrates the trabecular shunt of FIG. 3A at a semi-deployment state.
Figure 4B:
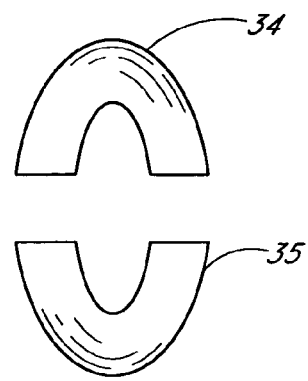
FIG. 4B is an end cross-sectional view of section 2-2 of FIG. 4A.

FIG. 4A shows the trabecular shunt of FIG. 3A in a semi-deployed state, while FIG. 4B shows an end cross-sectional view of section 2-2 of FIG. 4A. In one embodiment for shunt delivery, the trabecular shunt 31 is placed inside a hollow delivery apparatus 45. A delivery apparatus 45 comprises a distal end 47, wherein the two bifurcatable elements 34, 35 of the outlet section are self-bifurcatable in substantially two opposite directions when the trabecular shunt 31 is deployed out of the delivery apparatus 45. The slit 38 at the two bifurcatable elements 34, 35 comprises the separating regions 43A and 43B. The delivery apparatus 45 may comprise a deployment mechanism for deploying the trabecular shunt out of the delivery apparatus. In one embodiment, the deployment mechanism is a plunger. The delivery mechanism may be located at the handle of the delivery apparatus for deploying the trabecular shunt.

Figure 5A:
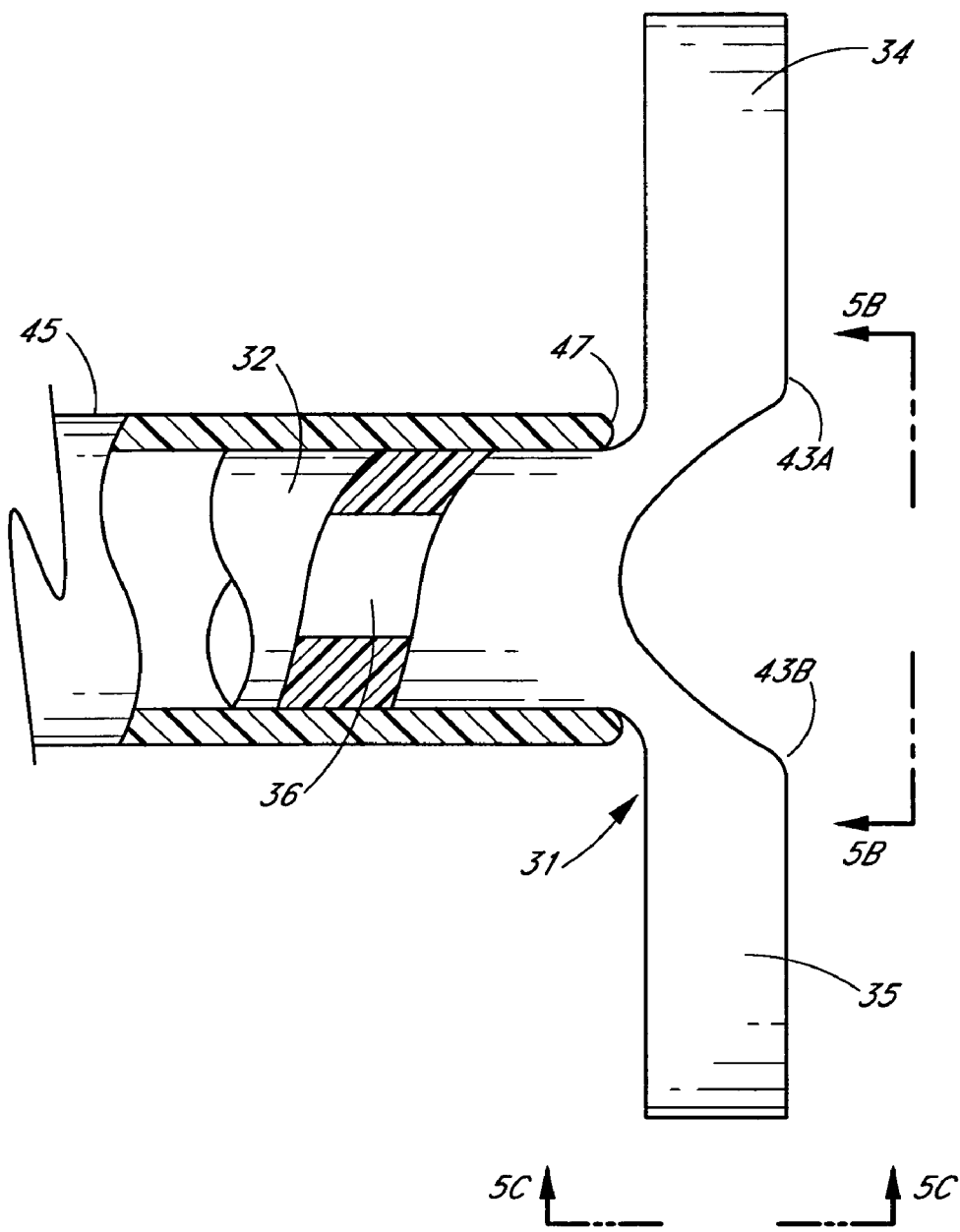
FIG. 5A illustrates the trabecular shunt of FIG. 3A in a deployed state.

FIG. 5A shows the trabecular shunt of FIG. 3A at a deployed state. As the plunger is continuously pushed ahead, and the distal end 47 of the delivery apparatus 45 retreats, the two bifurcatable elements 34, 35 continue to deploy in two substantially opposite directions. This may be accomplished by precontracting the two bifurcatable elements within the delivery apparatus before the delivery state. When the distal end of the delivery apparatus withdraws beyond the joint point 37 located between the inlet section 32 and the outlet section, the two bifurcatable elements are fully deployed with their separating regions 43A, 43B apart from each other. The outlet section of the trabecular shunt may be made of a material form selected from a group comprising coil form, mesh form, spiral form, porous form, semi-permeable form, fishbone form, continuous solid form, or any form that is effective and appropriate to evert the bifurcatable elements to be at one or more angles with respect to a reference axis of the inlet section.

Figure 5B:
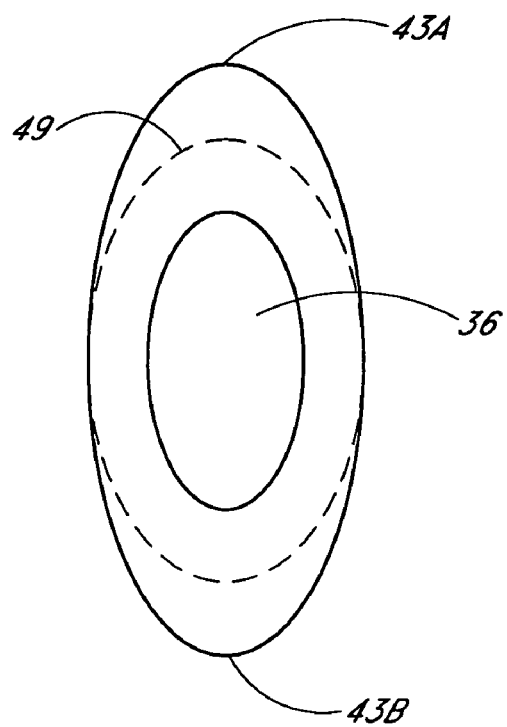
FIG. 5B is an end cross-sectional view of the trabecular shunt, section 3-3 of FIG. 5A.
Figure 5C:
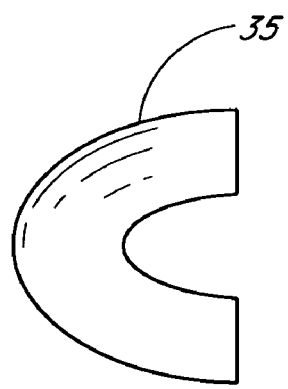
FIG. 5C is an end cross-sectional view of a bifurcatable segment, section 4-4 of FIG. 5A.

FIG. 5B shows an end cross-sectional view of the trabecular shunt, section 3-3 of FIG. 5A, while FIG. 5C shows an end cross-sectional view of a bifurcatable segment, section 4-4 of FIG. 5A. The original outer contour of the trabecular shunt 31 is illustrated by a dashed line 49 in FIG. 5B. The lumen 36 of the hollow elongated tubular element is for aqueous to flow through the trabecular shunt. The shape of the end cross-section 35 is to provide a stenting capability when the elements are placed inside Schlemm's canal. The semicircular end cross-section of the bifurcatable elements 34, 35 allows aqueous to freely flow into aqueous collector channels in the external wall of Schlemm's canal.

Figure 6:
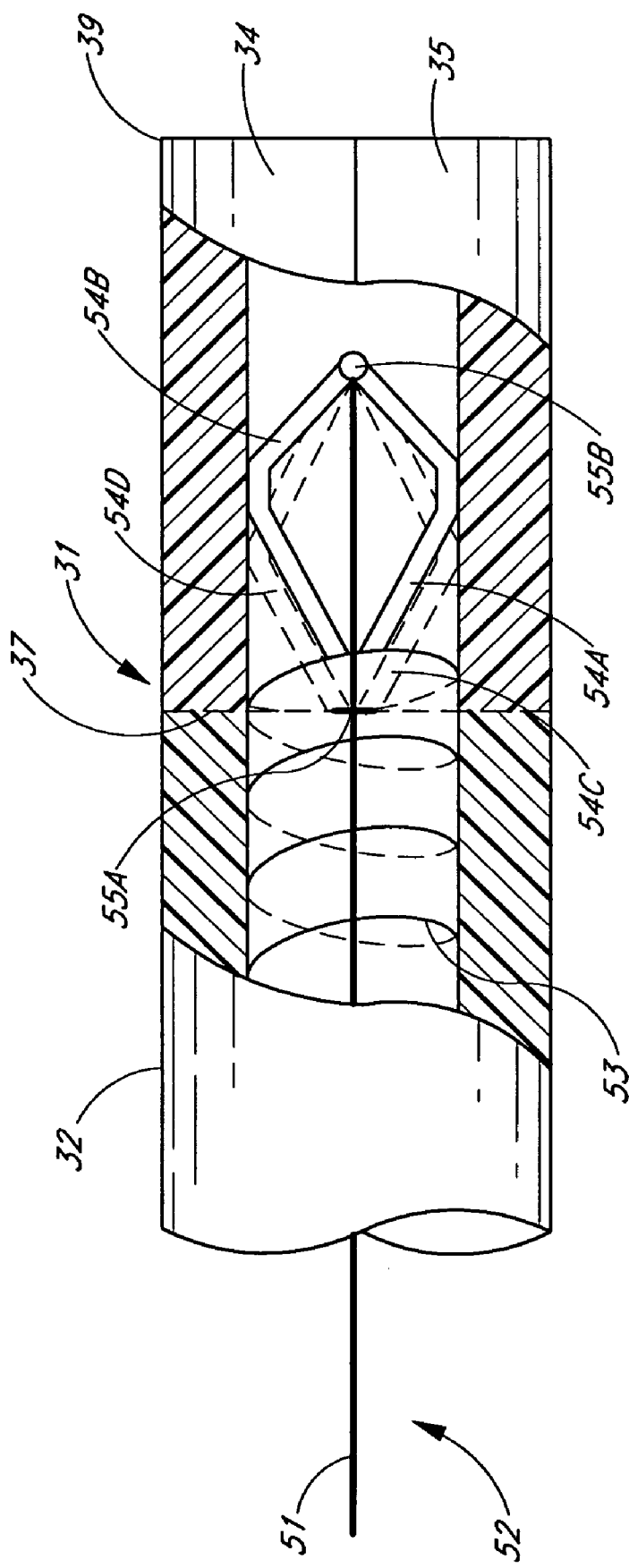
FIG. 6 is a side cross-sectional view of the trabecular shunt.

FIG. 6 shows another preferred embodiment of the trabecular shunt constructed according to the principles of the invention. A delivery applicator 52 may be placed inside a lumen of the hollow elongated tubular element, wherein the delivery applicator 52 comprises a deployment mechanism for effecting the two bifurcatable elements 34, 35 of the outlet section to substantially two opposite directions. The delivery applicator may be selected from a group comprising a guidewire, an expandable basket, an inflatable balloon, or other expanding mechanism. In one embodiment, a delivery applicator 52 with an expandable basket comprises a plurality of expandable members 54A, 54B, 54C, 54D that all securely joined at a proximal joint 55A and at a distal joint point 55B. A distal end of a push-pull type wire 51 is also joined at the distal joint point 55B. The proximal joint 55A is located at the distal end of a compact guidewire 53 of the delivery applicator. Therefore, by pulling the push-pull wire 51 of the delivery applicator toward the operator, each of the expandable members 54A, 54B, 54C, 54D expand radially outwardly so as to effect the outward pushing action for the bifurcatable elements 34, 35.

U.S. Pat. No. 6,077,298 and U.S. patent application Ser. No. 09/452,963, filed Dec. 2, 1999, the entire contents of which are incorporated herein by reference, disclose a medical device made of shape-memory Nitinol having a shape-transition temperature. The shape-memory material may be used in the construction of a trabecular shunt 31. In one embodiment, a trabecular shunt comprises a hollow elongated tubular element having an inlet section and an outlet section, wherein the outlet section comprises two bifurcatable elements adapted to be positioned and stabilized inside Schlemm's canal. At least one of the two bifurcatable elements may be made of a shape-memory material such as shape-memory Nitinol or shape-memory plastic material. In a preferred embodiment, the shape-memory Nitinol has a preshape and a shape-transition temperature, wherein the shape-memory Nitinol bifurcates to its preshape when the shape-memory Nitinol is heated to above the shape-transition temperature, the preshape of the shape-memory Nitinol being at an angle with respect to the inlet section.

The shape-transition temperature for the shape-memory Nitinol is preferably between about 39° C. and about 90° C. The shape-transition temperature is more preferred between about 39° C. and 45° C. so as to minimize tissue damage. The angle between the inlet section and the outlet section is preferably between about 70 degrees and about 110 degrees so as to conform to the counter of Schlemm's canal. An external heat source may be provided and adapted for heating the shape-memory Nitinol to above the shape-transition temperature of the shape-memory Nitinol. Examples of such external heat sources include a heating pad, a warm cloth, a bag of warm water, remotely deliverable heat, electromagnetic field, and the like. In another embodiment, the shape-memory Nitinol may be embedded within a biocompatible material selected from, for example, silicone, polyurethane, porous material, expanded polytetrafluoroethylene, semi-permeable membrane, elastomer, and mixture of the biocompatible material thereof. In general, the bifurcatable elements are relatively flexible and soft so that they do not impart undesired force or pressure onto the surrounding tissue during and after the deployment state.

Figure 7A:
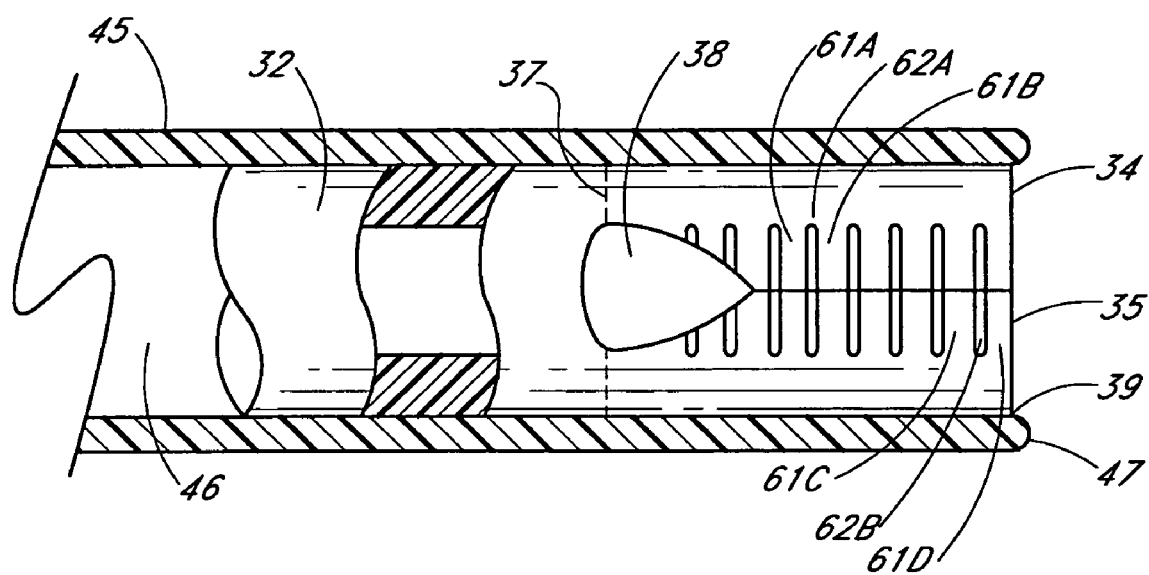
FIG. 7A is a side cross-sectional view of an alternate embodiment of the trabecular shunt.

For illustration purposes, a fishbone type outlet section is shown to render the bifurcatable elements flexible and soft during the deployment state. FIG. 7A shows an embodiment of the trabecular shunt constructed according to principles of the invention. The trabecular shunt comprises a plurality of fishbones and their intermediate spacing, such as the fishbones 61A, 61B with a spacing 62A and the fishbones 61C, 61D with a spacing 62B. A delivery apparatus 45 may be used to deliver the self-bifurcatable elements 34, 35 having fishbones configuration.

Figure 7B:
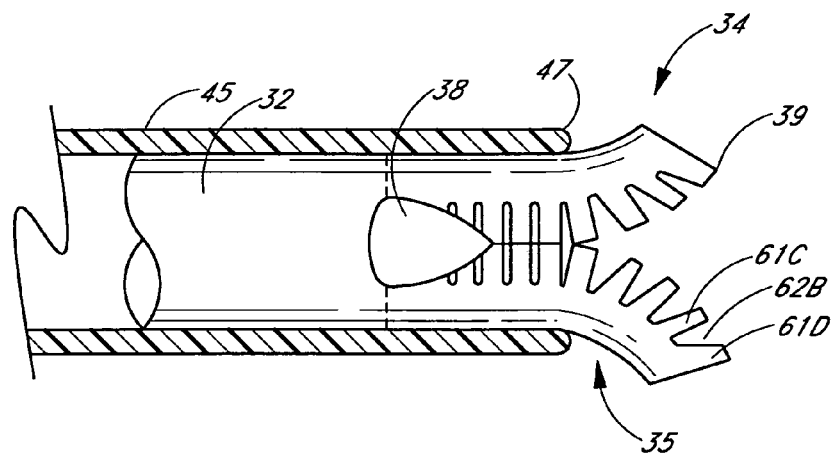
FIG. 7B is a side cross-sectional view of the trabecular shunt of FIG. 7A in a partially deployed state.

FIG. 7B shows the trabecular shunt of FIG. 7A in a semi-deployed state. As the distal end 47 of the delivery apparatus 45 is pulled away from the distal end 39 of the shunt 31, the self-bifurcatable elements 34, 35 tend to deploy to two opposite directions. In the meantime, the spacing 62B between the two fishbones 61C and 61D starts to expand and enlarge so that minimal stress is exerted on the deployed bifurcated portion of the bifurcatable elements 34, 35.

The trabecular shunt of the present invention may have a length between about 0.5 mm to over a few millimeters. The outside diameter of the trabecular shunt may range from about 30 μm to about 500 μm or more. The lumen diameter is preferably in the range of about 20 μm to about 150 μm, or larger. The trabecular shunt may have a plurality of lumens to facilitate multiple-channel flow. The outlet section may be curved or angled at an angle between about 30 degrees to about 150 degrees, and preferably at about 70 degrees to about 110 degrees, with reference to the inlet section 32.

Figure 8A:
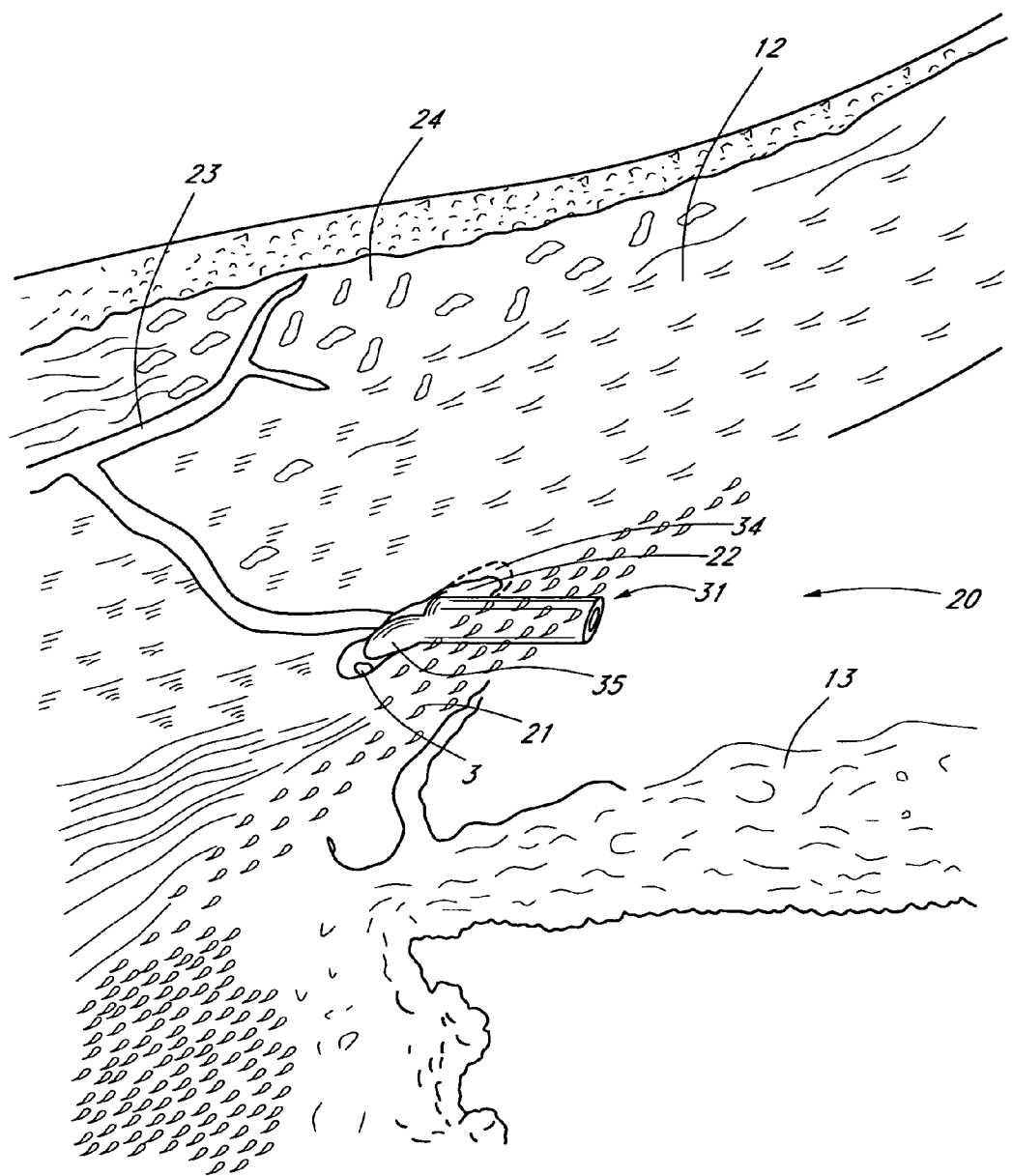
FIG. 8A is a perspective view of the trabecular shunt placed inside Schlemm's canal.

FIG. 8A is a perspective view illustrating the device 31 of the present invention positioned within the tissue of an eye 10. A hole or opening is created through the diseased trabecular meshwork 21. The outlet section of the device 31 is inserted into the hole, wherein the inlet section is exposed to the anterior chamber 20 while the outlet section is positioned at about an exterior surface 3 of the diseased trabecular meshwork 21. In a further embodiment, the outlet section may enter into Schlemm's canal or other existing outflow pathways. A device as shown in FIG. 3 may be successfully used to maintain the opening through diseased trabecular meshwork.

In one embodiment, means for forming a hole/opening in the trabecular meshwork 21 may comprise using a microknife, a pointed guidewire, a sharpened applicator, a screw shaped applicator, an irrigating applicator, or a barbed applicator. Alternatively, the trabecular meshwork may be dissected off with an instrument similar to a retinal pick or microcurrette. The opening may alternately be created by retrograde fiberoptic laser ablation.

In a preferred embodiment of the trabecular meshwork surgery, the patient is placed in the supine position, prepped, draped and anesthesia obtained. In one embodiment, a small (generally less than 1-mm) self-sealing incision is made. Through the cornea opposite the shunt placement site, an incision is made in the trabecular meshwork with an irrigating knife. The shunt is then advanced through the corneal incision across the anterior chamber held in a delivery apparatus or delivery applicator under gonioscopic (lens) or endoscopic guidance. The apparatus or applicator is withdrawn from the patient and the surgery is concluded. The delivery apparatus or applicator may be within a size range of 20 to 40 gauge, and preferably about 30 gauge.

In a further alternate embodiment, a method for increasing aqueous humor outflow in an eye of a patient to reduce intraocular pressure therein may comprise the following: (a) creating an opening in trabecular meshwork; (b) inserting a trabecular shunt into the opening, wherein the trabecular shunt comprises a hollow elongated tubular element having an inlet section and an outlet section, and wherein the outlet section comprises two bifurcatable elements adapted to be positioned and stabilized inside Schlemm's canal; and (c) bifurcating the two bifurcatable elements to substantially two opposite directions.

The method may further comprise placing the trabecular shunt inside a delivery apparatus during a delivery state, wherein the two bifurcatable elements are self-bifurcatable in two substantially opposite directions when the trabecular shunt is deployed from the delivery apparatus. The method may further comprise placing a delivery applicator inside a lumen of a hollow elongated tubular element, wherein the delivery applicator comprises a deployment mechanism for causing the two bifurcatable elements to move in two substantially opposite directions.

The method may further comprise measuring and transmitting pressure of the anterior chamber of an eye, wherein the trabecular shunt comprises a pressure sensor for measuring and transmitting pressure. The means for measuring and transmitting pressure of an anterior chamber of an eye to an external receiver may be incorporated within a device that is placed inside the anterior chamber for sensing and transmitting the intraocular pressure. Any suitable micro pressure sensor or pressure sensor chip known to those of skill in the art may be utilized.

Figure 8B:
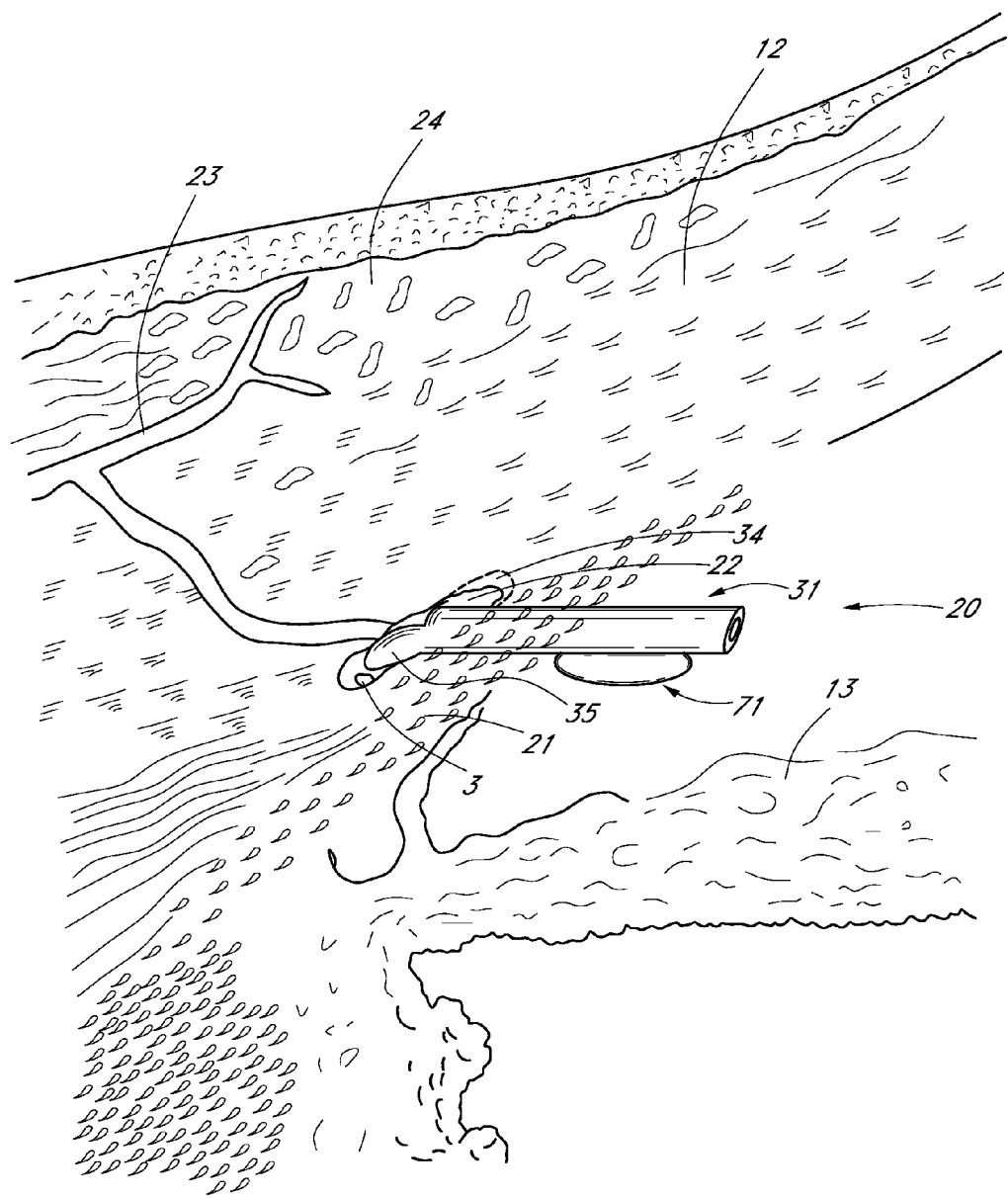
FIG. 8B is a perspective view of the trabecular shunt coupled to a passive IOP pressure sensor and placed inside Schlemm's canal.
Figure 9:
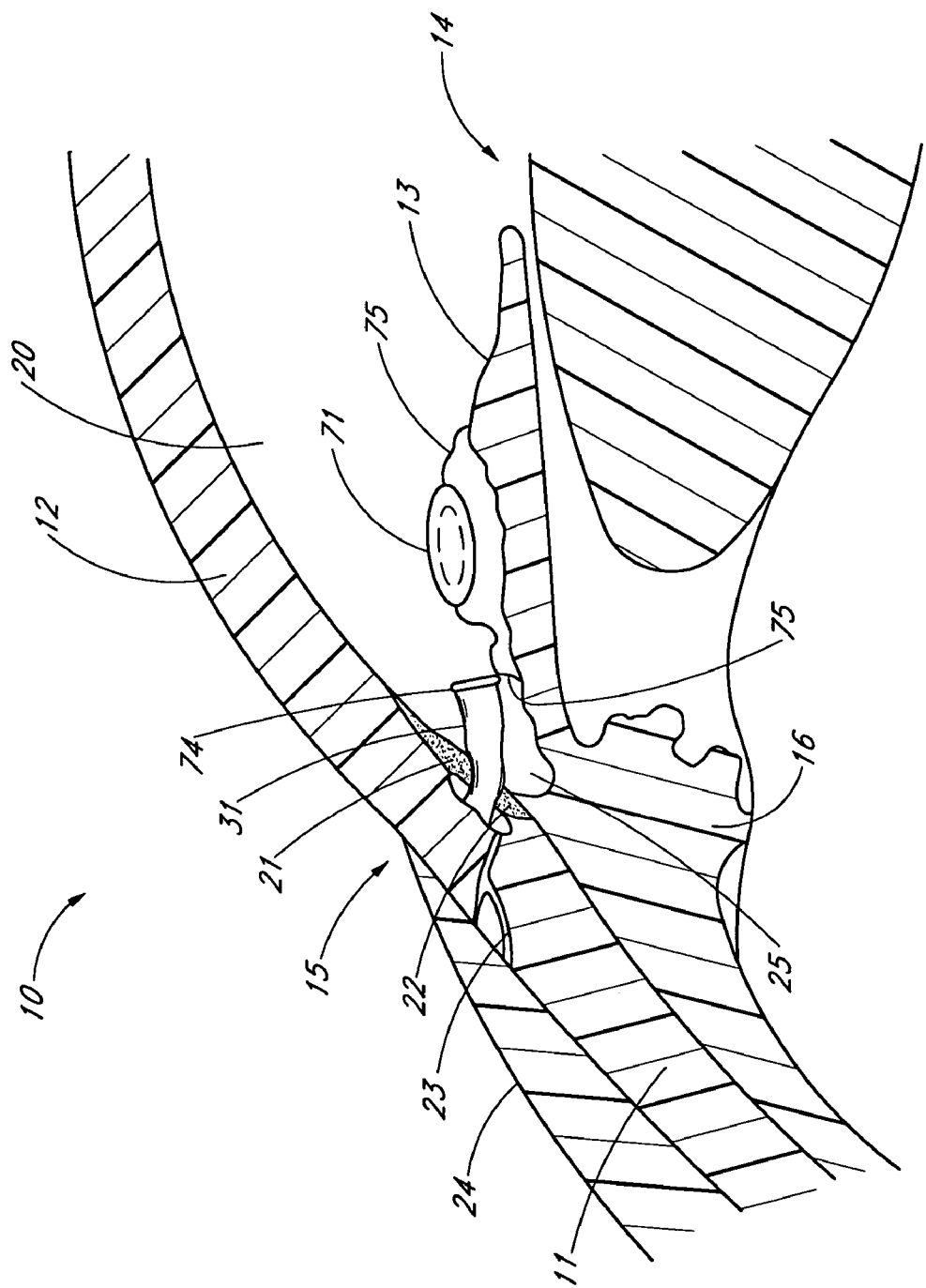
FIG. 9 is a close-up sectional view of the eye, showing the anatomical diagram of trabecular meshwork and the anterior chamber of the eye.

As shown in FIG. 9, the trabecular meshwork 21 constitutes a small portion of the sclera 11. It is understandable that creating a hole or opening for implanting a device through the tissues of the conjunctiva 24 and sclera 11 is relatively a major surgery as compared to a surgery for implanting a device through the trabecular meshwork 21. In one embodiment, a passive IOP sensor element 71 is secured to an iris 13 with at least one anchoring member 75 to prevent the element from randomly floating inside the anterior chamber. The sensor element is typically positioned out of the line of vision. In another embodiment, the IOP sensor element 71 may be coupled to the trabecular shunt 31, as shown in FIG. 8B. This may permit implantation of both the trabecular shunt 31 and the pressure sensor in a single procedure. The sensor may be coupled by any means know by those of skill in the art. For example, the sensor may be coupled to the trabecular shunt 31 by adhesive, soldering, etc. In some embodiments, the sensor may be integrally formed with the trabecular shunt 31.

FIG. 9 shows a trabecular stent system for glaucoma treatment, the stent system comprising: an elongate tubular implant 31 extending between an anterior chamber 20 and Schlemm's canal 22 for transporting fluid from said anterior chamber to said Schlemm's canal of an eye; and an intraocular pressure sensor 71 in association with the implant 31, said sensor comprising a compressible element, wherein at least one external dimension of the element is correlated to compressing pressure reading. The trabecular stent system further comprises a signal transmitter 74 (for example, a radiofrequency signal transmitter), said transmitter transmitting a sensed signal from said sensor 71 indicative of the sensed pressure to a receiver. The receiver may be located outside of the eye or inside the eye.

The IOP sensor element can comprise a biocompatible material, such as a medical grade silicone, for example, the material sold under the trademark Silastic™, which is available from Dow Corning Corporation of Midland, Mich., or polyurethane, which is sold under the trademark Pellethane™, which is also available from Dow Corning Corporation. In an alternate embodiment, at least a portion of the sensor element can comprise other biocompatible materials (biomaterials), such as polyvinyl alcohol, polyvinyl pyrolidone, collagen, heparinized collagen, tetrafluoroethylene, fluorinated polymer, fluorinated elastomer, flexible fused silica, polyolefin, polyester, polysilicon, mixture of biocompatible materials, and the like. In a further alternate embodiment, a composite biocompatible material by surface coating the above-mentioned biomaterial can be used, wherein the coating material may be selected from a group consisting of polytetrafluoroethylene (PTFE), polyimide, hydrogel, heparin, therapeutic drugs, and the like.

Some embodiments relate to an intraocular pressure sensor comprising a compressible element that is implanted inside an anterior chamber of an eye, wherein at least one external dimension of the element is correlated to a compressing pressure reading, and an external measuring means for remotely viewing and measuring the at least one external dimension of the element. Some embodiments provide a pressure sensor element 71 in response to a remote sensing and measuring instrument for measuring the IOP indirectly. In this embodiment, the sensor element does not need supplemental energy or electromechanical means for powering the sensor element. It is thus a passive IOP sensing device.

Figure 10:
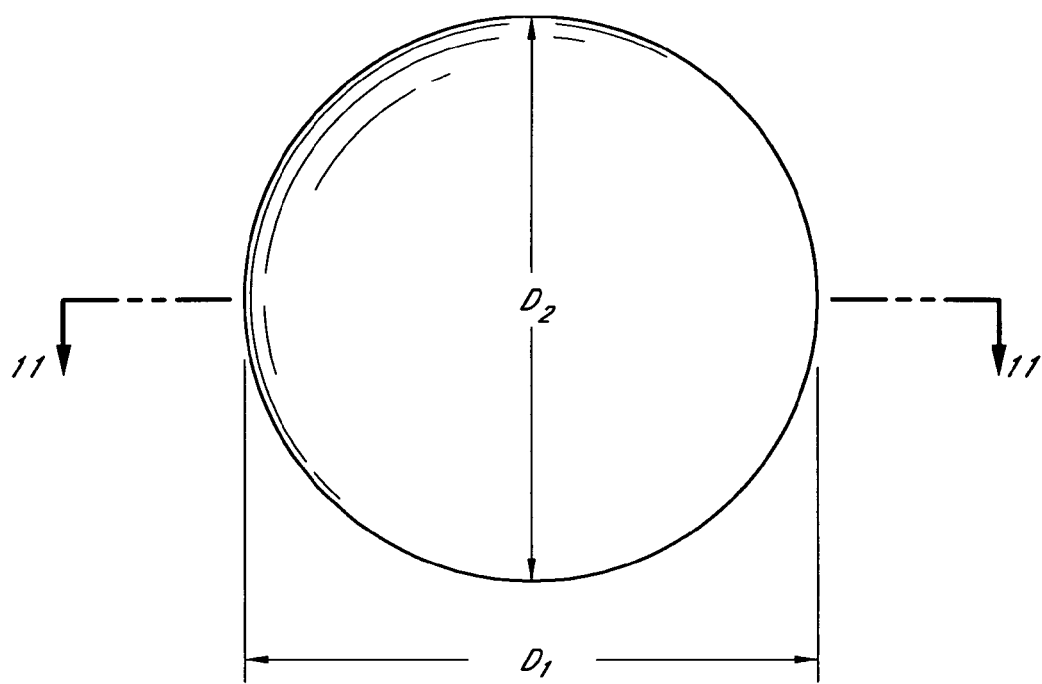
FIG. 10 shows one embodiment of a passive IOP pressure sensor element.
Figure 11:
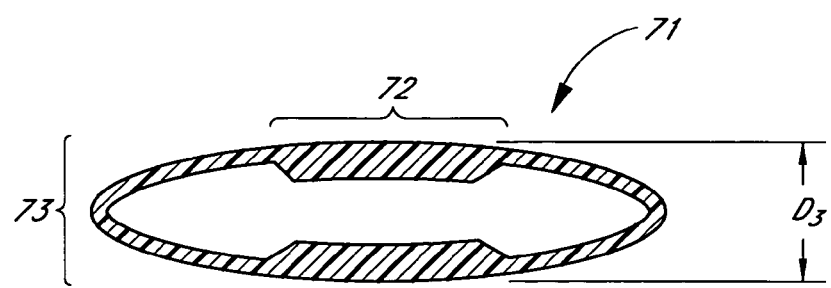
FIG. 11 is a cross-sectional view, section 5-5 of FIG. 10.

FIG. 10 shows one embodiment of a passive IOP pressure sensor element 71, while FIG. 11 shows a cross-sectional view, section 5-5 of FIG. 10. The passive pressure sensor element 71 may be anchored or secured to a tissue of the eye. For example, the pressure sensor element 71 may be anchored to the iris 13 of the eye, as shown in FIG. 9. The element may be attached to a trabecular stent implant, as shown in FIG. 8B. The sensor element is sized, dimensioned and configured to be suitably implanted inside the eye out of the line of vision and visible to the external measuring means. Although FIG. 8B illustrates an embodiment in which the pressure sensor element 71 is located underneath (posterior to) the trabecular shunt 31, the pressure sensor element 71 may be placed at any location on the shunt 31. In one embodiment, the pressure sensor element 71 is located above the trabecular shunt 31 to permit external observation of the shunt 31. In one embodiment, the longest dimension of the element is less than about 1 cm, preferably less than about 5 mm. In other embodiments, however, the longest dimension of the element may be greater than about 1 cm or less than about 5 mm. In one embodiment, the sensor element is made of compressible membrane material that will respond to varying pressures in the eye.

In one preferred embodiment, the IOP pressure sensor element 71 comprises an enclosure with compressible fluid (for example, a gas) entrapped within the enclosure. The sensor element 71 has a length $D_2$, a width $D_1$ and a depth $D_3$ as shown in FIGS. 10 and 11. In some embodiments, the sensor element 71 is sized, constructed, and configured so the compressing pressure affects the change of the width $D_1$ (in the illustrated case, $D_1$ is equal to $D_2$) while not appreciably affecting dimension $D_3$. The passive IOP sensor element 71 is precalibrated to show a correlation of the width $D_1$ or length $D_2$ as a function of the compressing pressure (designated as P). In another embodiment, the IOP sensor element 71 is precalibrated to provide a correlation of the width change (designated as $\Delta D_1$) as a function of the compressing pressure change (designated as $\Delta P$).

In one embodiment, the edge portion 73 along the width $D_1$ is more pressure-sensitive than the central portion 72 along the width $D_1$ enabling viewing the total width as a function of compressing pressure by a physician. In this embodiment, a greater pressure in the eye would result in a change of length in the width $D_1$ along the edge portion 73 of the sensor 71 than the change of the central portion 72. In some embodiments, the construction material at the edge portion can be different from that at the central portion. In another embodiment, the thickness at the edge portion 73 can be different from that at the central portion 72. In a further embodiment, the shape and size of the passive IOP sensor element 71 is suitably configured to yield the precalibrated correlation of the dimensions of the sensor 71 as a function of the compressing pressure (designated as P). Some embodiments relate to an IOP sensor element comprising a compressible enclosure, wherein compressible gas is enclosed within the enclosure, and wherein a dimension of the enclosure is correlated with a compressing pressure.

A compressible element of the ellipsoid shape has a major diameter $D_1$ and a minor diameter $D_3$ (similar to the one shown in FIGS. 10 and 11 with $D_1=D_2$). Place the element inside a compressing pressure chamber with a pressure reading. The dimension $D_1$ is read as a function of the compressing pressure P as follows:

| Reading # | $D_1$ length, mm | Compressing pressure, mmHg |
|---|---|---|
| 1 | 5.0 | 10.0 |
| 2 | 4.9 | 11.5 |
| 3 | 4.8 | 13.2 |
| 4 | 4.7 | 15.2 |
| 5 | 4.6 | 17.7 |
| 6 | 4.5 | 20.7 |
| 7 | 4.4 | 24.4 |
| 8 | 4.2 | 39.4 |

Figure 12:
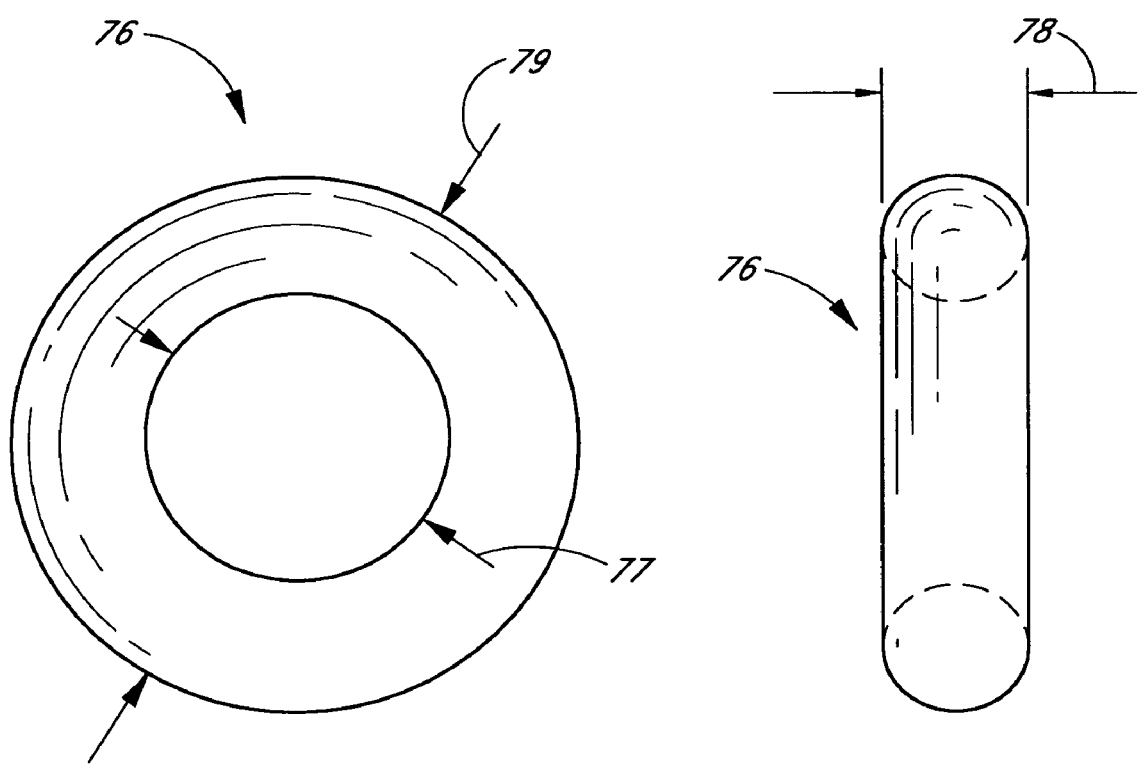
FIG. 12 shows another embodiment of a passive IOP pressure sensor element.

FIG. 12 shows another embodiment of a passive IOP pressure sensor element 76. In one embodiment, the IOP pressure sensor or sensor element may have unilateral expansion or shrinkage of primarily a single diameter that takes place with the sphere. In another embodiment, two or more dimensions change in response to external pressure fluctuations. In the ellipsoid enclosure, (such as the one shown in FIGS. 10 and 11) both the major diameter $D_1$ and the minor diameter $D_3$ may change in response to external pressure fluctuations. Measuring pressure with the ellipsoid involves taking a measurement, preferably, of the major or greater diameter $D_1$. The major diameter of the ellipsoid is truly visible from any potential angle of projection by locating the single farthest distance between opposing outer surfaces on the ellipsoid on a line that passes through the center. The distance thus measured is plotted onto a calibration curve showing the major diameter vs. external pressure for the specific ellipsoid and the corresponding pressure reading.

In a preferred embodiment, the IOP pressure sensor is substantially a sphere in shape, rather than being elliptical. In this spheroid embodiment (not shown), the dimensions $D_1$, $D_2$, and $D_3$ are substantially equal. This embodiment has the advantage of compressing substantially equally in all or nearly all dimensions in response to an increase in intraocular pressure, so one may perhaps easily measure a diameter in order to obtain a reading that correlates with IOP.

In the case of a compressible tubular wheel (such as a torus) as shown in FIG. 12, the thickness 78, the outer diameter 79, and the inner diameter 77 change as a function of external pressure. In one embodiment, the changes in the thickness, the outer diameter and the inner diameter are relatively uniform, wherein uniform changes in these dimensions assume that the bodies are sized and constructed so that pressure changes affect uniform and smooth dimensional changes in most or all dimensions. Measuring pressure with the torus involves measuring the outer diameter 79. The outer diameter of the torus is visible from any potential angle of projection by locating the single farthest distance between the opposing outer surfaces on the torus on a line that passes through the center. The distance thus measured is plotted onto a calibration curve showing the outer diameter vs. external pressure for the specific torus and the corresponding pressure reading. Alternately, the inner diameter can also be measured by viewing the maximum dimension and ensuring that the outside diameter is not mistakenly captured.

In one embodiment, the passive IOP sensor element is a sphere, a spherical ball, an ellipsoid ball, a torus type spherical tube or other dimensional element, preferably a nearly perfect sphere, whose sphere diameter changes in all directions uniformly with a change in external pressure. In a further embodiment, the sphere could be situated and viewed from any angle. The sphere could float in the eye, on a tether perhaps, and still be accurately sensed without elaborate positioning requirements. The spheres or element 71, 76 are biocompatible and suitable for implantation in an eye.

In one embodiment, at least a part of the surface of the enclosure is rendered radiopaque for X-ray visualization. In another embodiment, at least a part of the surface of the enclosure is colored or coated with a visualizable material for external signal viewing. The external means for remotely viewing and measuring the at least one external dimension of the element can be a slit lamp, an ultrasound imaging apparatus, a laser light apparatus, the X-ray imaging apparatus or the like. The enclosure with enclosed gas is also visible by ultrasound.

Figure 7C:
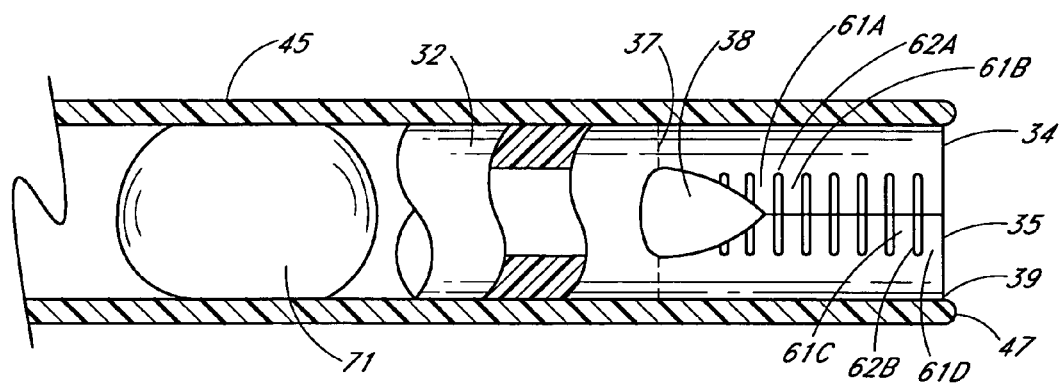
FIG. 7C is a side cross-sectional view of the trabecular shunt and a passive IOP pressure sensor loaded in series in a delivery device.
Figure 13:
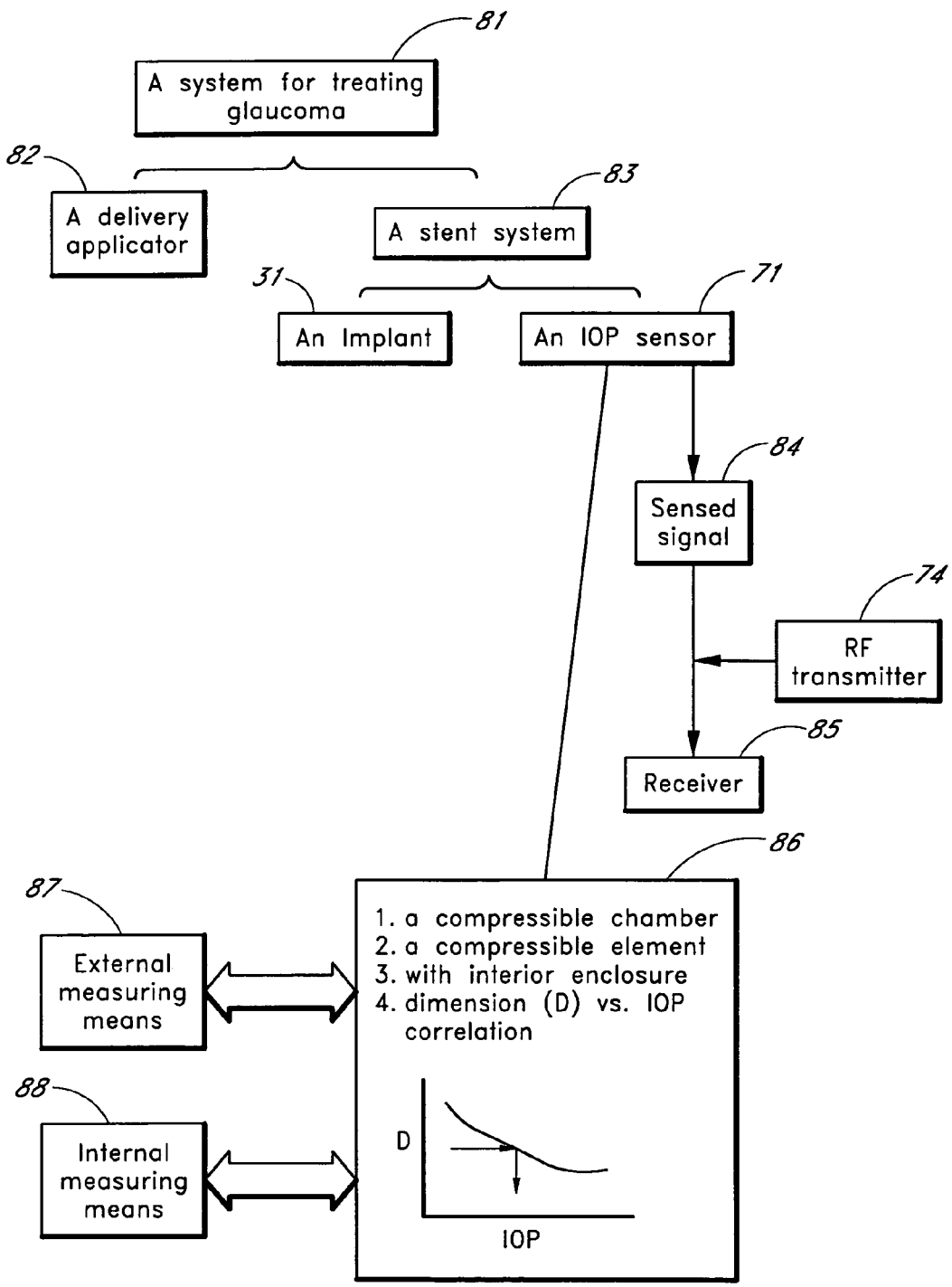
FIG. 13 shows a block diagram for a glaucoma treatment system.

FIG. 13 shows a block diagram for a glaucoma treatment system of the present invention. Some aspects of the invention relate to a system for treating glaucoma 81. The system may comprise an intraocular pressure sensor 71 that comprises a compressible element 86 with at least one external dimension of the element is configured to be correlated to the compressing pressure reading. The system may further comprise an elongate tubular implant 31 for transporting fluid between an anterior chamber and Schlemm's canal and a delivery applicator 82. The intraocular pressure sensor and the implant may be positioned within said delivery applicator for delivering into the anterior chamber for implantation. In some embodiments, the intraocular pressure sensor 71 and the implant 31 may be serially contained in the delivery applicator to permit application of the implant 31 and the sensor 71 in one procedure, as shown in FIG. 7C. This may permit implantation of the implant 31 and the sensor 71 without the need for discreet delivery applicators or incisions in the eye. The operation of the delivery applicator may be the similar to that described above with respect to the delivery applicator of the implant 31 in FIGS. 6-7B.

Some aspects of the invention relate to a trabecular stent system 83 for glaucoma treatment, the stent system may comprise an elongate tubular implant that is configured to extend between an anterior chamber and Schlemm's canal for transporting fluid from said anterior chamber to said Schlemm's canal of an eye. The system may also comprise an intraocular pressure sensor in association with the implant, and the sensor may comprise a compressible element that has at least one external dimension that is correlated to compressing pressure reading (as shown in a relationship figure in the block 86). The trabecular stent system may further comprise a signal transmitter (such as a radiofrequency transmitter 74), and the transmitter may transmit a sensed signal 84 from the sensor indicative of the sensed pressure to a receiver 85. The receiver may be located either outside of the eye or inside the eye.

In a co-pending application Ser. No. 10/910,962, filed Aug. 4, 2004, entitled "Implantable Ocular Pump to Reduce Intraocular Pressure," the entire contents of which are incorporated herein by reference, disclosed are energy sources for powering a micropump on a trabecular stent. In a co-pending application Ser. No. 10/636,797, filed Aug. 7, 2003, entitled "Implantable Ocular Pump to Reduce Intraocular Pressure," the entire contents of which are incorporated herein by reference, disclosed is conversion of mechanical stress, such as a group comprising blink pressure pulses, ocular pressure pulses, body motion, head motions, and eye motions, to piezoelectricity.

Some embodiments relate to a method for measuring an intraocular pressure of an eye that may comprise the following: (a) provide a compressible element that is implanted inside an anterior chamber of the eye, wherein at least one external dimension of the element is correlated to compressing pressure reading; (b) implanting the element inside the eye; (c) using an external measuring means for remotely viewing and measuring the at least one external dimension of the element; and (d) calculating the intraocular pressure of the eye by correlating the measured external dimension to the compressing pressure reading.

From the foregoing description, it should be appreciated that a novel approach for the surgical treatment of glaucoma has been disclosed for reducing IOP and sensing and measuring IOP from outside of the eye has been disclosed for measuring intraocular pressure. While the invention has been described with reference to specific embodiments, the description is illustrative of the invention and is not to be construed as limiting the invention. Various modifications and applications of the invention may occur to those who are skilled in the art, without departing from the true spirit or scope of the invention. The breadth and scope of the invention should be defined only in accordance with the appended claims and their equivalents.

What is claimed is:

1. A method of treating and monitoring of glaucoma, the method comprising:
   providing a delivery device configured to be inserted into an eye of a patient;
   providing at least one implant, the implant configured to be held within the delivery device, and the implant comprising:
      an inlet and an outlet section, the inlet section being in fluid communication with the outlet section and configured to conduct fluid from an anterior chamber of the eye to Schlemm's canal of the eye;
   providing a sensor element configured to measure intraocular pressure and configured to be held within the delivery device;
   positioning the at least one implant in the eye such that an end of the inlet section is in the anterior chamber of the eye and an end of the outlet section is in Schlemm's canal;
   positioning the sensor element completely within the anterior chamber of the eye to measure the intraocular pressure of the eye; and
   anchoring, from within the anterior chamber, the sensor element to eye tissue such that the sensor element is spaced apart from the implant.

2. The method of claim 1, wherein the delivery device comprises a lumen extending through at least a portion thereof.

3. The method of claim 1, wherein the delivery device comprises a tube.

4. The method of claim 3, wherein the implant and sensor element are preloaded in the tube.

5. The method of claim 1, wherein at least one of either the sensor element or the implant are preloaded in or on the delivery device.

6. The method of claim 1, further comprising inserting the implant into the eye through an incision in the eye and inserting the sensor element into the eye through the same incision in the eye.

7. The method of claim 1, wherein positioning the at least one implant in the eye comprises positioning a portion of the at least one implant in trabecular meshwork of the eye.

8. A method of monitoring intraocular pressure comprising:
   providing a delivery device configured to be inserted into at least an anterior chamber of an eye of a patient;
   providing at least one implant, the implant being held within the delivery device and comprising a proximal end portion and a distal end portion;
   providing a sensor element configured to measure intraocular pressure and being held within the delivery device;
   inserting the delivery device into the anterior chamber;
   positioning the at least one implant in the eye such that the distal end portion of the implant extends through eye tissue and the proximal end portion is disposed within the anterior chamber;
   positioning the sensor element completely within the anterior chamber of the eye to measure the intraocular pressure of the eye;
   substantially fixing, from within the anterior chamber, the sensor element to ocular tissue such that the sensor element is spaced apart from the implant; and
   conducting aqueous humor through the implant from the anterior chamber to a physiologic outflow pathway.

9. The method of claim 8, wherein positioning the implant involves inserting at least a portion of the distal end portion into Schlemm's canal of the eye.

10. The method of claim 8 additionally comprising forming an incision in the cornea of the eye, inserting the sensor element into the anterior chamber through the incision, and advancing the sensor element across the anterior chamber.

* * * * *

UNITED STATES PATENT AND TRADEMARK OFFICE
CERTIFICATE OF CORRECTION

| | |
|---|---|
| PATENT NO. | : 7,678,065 B2 |
| APPLICATION NO. | : 10/950175 |
| DATED | : March 16, 2010 |
| INVENTOR(S) | : David S. Haffner et al. |

It is certified that error appears in the above-identified patent and that said Letters Patent is hereby corrected as shown below:

Title page Item (56), page 3, column 2, line 10, under Other Publications, change "Cronic" to --Chronic--.

Title page Item (56), page 3, column 2, line 22, under Other Publications, change "Lasesr" to --Laser--.

Title page Item (56), page 3, column 2, line 29, under Other Publications, change "Ophthalmololgy," to --Ophthalmology,--.

Title page Item (56), page 3, column 2, line 40, under Other Publications, change "Horst Laque," to --Horst Laqua,--.

Title page Item (56), page 3, column 2, line 41, under Other Publications, change "Anteriuor" to --Anterior--.

Title page Item (56), page 4, column 1, lines 13-14, under Other Publications, change "Pseudowdoliation" to --Pseudoexfoliation--.

Column 1, line 9, change "Now" to --now--.

Column 1, lines 58-59, change "juxtacanilicular" to --juxtacanalicular--.

Column 2, line 27, change "5-flurouracil" to --5-fluorouracil--.

Column 2, line 59, change "Neodymiun" to --Neodymium--.

Column 3, line 14, change "microcurrette" to --microcurette--.

Signed and Sealed this
Twenty-fifth Day of January, 2011

David J. Kappos
*Director of the United States Patent and Trademark Office*

CERTIFICATE OF CORRECTION (continued)
U.S. Pat. No. 7,678,065 B2

Column 3, line 18, change "viscocanulostomy" to --viscocanalostomy--.

Column 3, line 56, change "juxtacanilicular" to --juxtacanalicular--.

Column 5, line 12, change "pyrolidone," to --pyrrolidone,--.

Column 5, line 15, change "polysilison," to --polysilicon,--.

Column 5, line 16, change "hydroxyapetite," to -- hydroxyapatite,--.

Column 9, line 49, change "pyrolidone," to --pyrrolidone,--.

Column 9, lines 52-53, change "polysilison," to --polysilicon,--.

Column 9, line 54, change "hydroxyapetite," to --hydroxyapatite,--.

Column 13, line 13, change "microcurrette." to --microcurette.--.

Column 14, lines 32-33, change "pyrolidone," to --pyrrolidone,--.